US008383340B2

(12) United States Patent
Ketterer et al.

(10) Patent No.: US 8,383,340 B2
(45) Date of Patent: Feb. 26, 2013

(54) METHOD FOR PURIFYING RNA ON A PREPARATIVE SCALE BY MEANS OF HPLC

(75) Inventors: Thomas Ketterer, Tübingen (DE); Florian Von Der Mulbe, Stuttgart (DE); Ladislaus Reidel, Rottenburg (DE); Thorsten Mutzke, Reutlingen (DE)

(73) Assignee: Curevac GmbH, Tubingen (DE)

( * ) Notice: Subject to any disclaimer, the term of this patent is extended or adjusted under 35 U.S.C. 154(b) by 305 days.

(21) Appl. No.: 12/520,172

(22) PCT Filed: Dec. 20, 2007

(86) PCT No.: PCT/EP2007/011294
§ 371 (c)(1),
(2), (4) Date: Oct. 20, 2009

(87) PCT Pub. No.: WO2008/077592
PCT Pub. Date: Jul. 3, 2008

(65) Prior Publication Data
US 2010/0048883 A1    Feb. 25, 2010

(30) Foreign Application Priority Data
Dec. 22, 2006  (DE) ................. 10 2006 061 015

(51) Int. Cl.
*C12Q 1/68*    (2006.01)
*C07H 21/00*   (2006.01)

(52) U.S. Cl. .................. 435/6.1; 536/22.1; 536/25.4
(58) Field of Classification Search ................. 435/6.1; 536/23.1, 25.4, 22.1
See application file for complete search history.

(56) References Cited

U.S. PATENT DOCUMENTS

| 5,447,922 | A | 9/1995 | Lawrence et al. |
| 2002/0102563 | A1 | 8/2002 | Gjerde et al. |
| 2005/0011836 | A1 | 1/2005 | Bidlingmeyer et al. |
| 2005/0215777 | A1* | 9/2005 | Vargeese et al. ............ 536/25.33 |
| 2008/0033158 | A1* | 2/2008 | Ngo et al. .................. 536/25.4 |
| 2010/0189729 | A1* | 7/2010 | Hoerr et al. ............... 424/184.1 |
| 2010/0203076 | A1* | 8/2010 | Fotin-Mleczek et al. .. 424/193.1 |

FOREIGN PATENT DOCUMENTS

| CA | 2 468 048 A1 | 8/1995 |
| JP | 8073477 | 3/1996 |
| WO | WO 01/46687 | 6/2001 |

OTHER PUBLICATIONS

McFarland et al., Separation of oligo-RNA by reverse-phase HPLC. Nucleic Acids Research 7(4) : 1067 (1979).*
Wincott et al., Synthesis, deprotection, analysis and purification of RNA and ribozymes. Nucleic Acids Research 23(14):2677 (1995).*
Zou et al., Engineered RNase P ribozymes are efficient in cleaving a human cytomegalovirus mRNA in vitro and are effective in inhibiting viral gene expression and growth in human cells. J. of Biological Chemistry 278 (39) :37265 (2003).*
Dickman, M.J. et al., "Enrichment and Analysis of RNA Centered on Ion Pair Reverse Phase Methodolo." *RNA*, vol. 12, No. 4, Apr. 2006, pp. 691-696.
Anderson, A.C. et al., "HPLC Purification of RNA for Crystallography and NMR." *RNA*, vol. 2, No. 2, 1996, pp. 110-117.
Azarani, A. et al., "RNA ANalysis by Ion-Pair Reversed-Phase High Performance Liquid Chromatography." *Nucleic Acids Research*, vol. 29, No. 2, Jan. 15, 2001, p. E7.
Georgopoulos, D.E., et al.: "Use of High-Performance Liquid Chromatographic Fractionation of Large RNA Molecules in the Assay of Group 1 Intron Ribozyme Activity," J. Chromatogr A, vol. 868(1), pp. 109-114, 2000.
Hashimoto: "Macroporous Synthetic Hydophilic Resin-Based Packings for the Separation of Biopolymers," J. Chromatogr, vol. 544, pp. 249-255, 1991.
Petro, et al., Molded continuous poly(styrene-co-divinylbenzene) rod as a separation medium for the very fast separation of polymers. Comparison of the chromatographic properties of the monolithic rod with columns packed with porous and non-porous beads in high-performance liquid chromatography of polystyrenes J. Chromatogr. A, Nov. 1, 1996, 752(1-2): 59-66.

* cited by examiner

*Primary Examiner* — Ethan C Whisenant
(74) *Attorney, Agent, or Firm* — Fanelli Haag & Kilger PLLC

(57) ABSTRACT

The application describes a method for the preparative purification of RNA, which method is distinguished in that the RNA is purified by means of HPLC using a porous reversed phase as the stationary phase. The use of the porous reversed phase in this HPLC method is also described.

26 Claims, 16 Drawing Sheets

Luciferase wild type

CAP-Ppluc(wt)-muag-A70 mRNA-sequence:

```
   1 GGGAGAAAGC UUGGCAUUCC GGUACUGUUG GUAAAGCCAC CAUGGAAGAC
  51 GCCAAAAACA UAAAGAAAGG CCCGGCGCCA UUCUAUCCGC UGGAAGAUGG
 101 AACCGCUGGA GAGCAACUGC AUAAGGCUAU GAAGAGAUAC GCCCUGGUUC
 151 CUGGAACAAU UGCUUUUACA GAUGCACAUA UCGAGGUGGA CAUCACUUAC
 201 GCUGAGUACU UCGAAAUGUC CGUUCGGUUG GCAGAAGCUA UGAAACGAUA
 251 UGGGCUGAAU ACAAAUCACA GAAUCGUCGU AUGCAGUGAA AACUCUCUUC
 301 AAUUCUUUAU GCCGGUGUUG GGCGCGUUAU UUAUCGGAGU UGCAGUUGCG
 351 CCCGCGAACG ACAUUUAUAA UGAACGUGAA UUGCUCAACA GUAUGGGCAU
 401 UUCGCAGCCU ACCGUGGUGU UCGUUUCCAA AAAGGGGUUG CAAAAAAUUU
 451 UGAACGUGCA AAAAAAGCUC CCAAUCAUCC AAAAAAUUAU UAUCAUGGAU
 501 UCUAAAACGG AUUACCAGGG AUUUCAGUCG AUGUACACGU UCGUCACAUC
 551 UCAUCUACCU CCCGGUUUUA AUGAAUACGA UUUUGUGCCA GAGUCCUUCG
 601 AUAGGGACAA GACAAUUGCA CUGAUCAUGA ACUCCUCUGG AUCUACUGGU
 651 CUGCCUAAAG GUGUCGCUCU GCCUCAUAGA ACUGCCUGCG UGAGAUUCUC
 701 GCAUGCCAGA GAUCCUAUUU UUGGCAAUCA AAUCAUUCCG GAUACUGCGA
 751 UUUUAAGUGU UGUUCCAUUC CAUCACGGUU UUGGAAUGUU UACUACACUC
 801 GGAUAUUUGA UAUGUGGAUU UCGAGUCGUC UUAAUGUAUA GAUUUGAAGA
 851 AGAGCUGUUU CUGAGGAGCC UUCAGGAUUA CAAGAUUCAA AGUGCGCUGC
 901 UGGUGCCAAC CCUAUUCUCC UUCUUCGCCA AAAGCACUCU GAUUGACAAA
 951 UACGAUUUAU CUAAUUUACA CGAAAUUGCU UCUGGUGGCG CUCCCCUCUC
1001 UAAGGAAGUC GGGGAAGCGG UUGCCAAGAG GUUCCAUCUG CCAGGUAUCA
1051 GGCAAGGAUA UGGGCUCACU GAGACUACAU CAGCUAUUCU GAUUACACCC
1101 GAGGGGGAUG AUAAACCGGG CGCGGUCGGU AAAGUUGUUC CAUUUUUUGA
1151 AGCGAAGGUU GUGGAUCUGG AUACCGGGAA AACGCUGGGC GUUAAUCAAA
1201 GAGGCGAACU GUGUGUGAGA GGUCCUAUGA UUAUGUCCGG UUAUGUAAAC
1251 AAUCCGGAAG CGACCAACGC CUUGAUUGAC AAGGAUGGAU GGCUACAUUC
1301 UGGAGACAUA GCUUACUGGG ACGAAGACGA ACACUUCUUC AUCGUUGACC
1351 GCCUGAAGUC UCUGAUUAAG UACAAAGGCU AUCAGGUGGC UCCCGCUGAA
1401 UUGGAAUCCA UCUUGCUCCA ACACCCCAAC AUCUUCGACG CAGGUGUCGC
1451 AGGUCUUCCC GACGAUGACG CCGGUGAACU UCCCGCCGCC GUUGUUGUUU
1501 UGGAGCACGG AAAGACGAUG ACGGAAAAAG AGAUCGUGGA UUACGUCGCC
1551 AGUCAAGUAA CAACCGCGAA AAAGUUGCGC GGAGGAGUUG UGUUUGUGGA
1601 CGAAGUACCG AAAGGUCUUA CCGGAAAACU CGACGCAAGA AAAAUCAGAG
1651 AGAUCCUCAU AAAGGCCAAG AAGGGCGGAA AGAUCGCCGU GUAAUUCUAG
1701 UUAUAAGACU GACUAGCCCG AUGGGCCUCC CAACGGGCCC UCCUCCCCUC
1751 CUUGCACCGA GAAAAAAAAA AAAAAAAAAA AAAAAAAAAA AAAAAAAAAA
1801 AAAAAAAAAA AAAAAAAAAA AAAAA
```

Figure 9

METHOD FOR PURIFYING RNA ON A PREPARATIVE SCALE BY MEANS OF HPLC

RELATED APPLICATIONS

This application is a national stage application (under 35 U.S.C. §371) of PCT/EP2007/011294, filed Dec. 20, 2007, which claims benefit of German application 102006061015.6, filed Dec. 22, 2006.

SUBMISSION OF SEQUENCE LISTING

The Sequence Listing associated with this application is filed in electronic format via EFS-Web and hereby incorporated by reference into the specification in its entirety. The name of the text file containing the Sequence Listing is Sequence_Listing_22122_00029US. The size of the text file is 3 KB, and the text file was created on Jun. 8, 2009.

The present invention relates to a method for purifying RNA on a preparative scale by means of HPLC and to the use of a porous reversed phase as stationary phase in this method.

HPLC (abbreviation for "High Performance (High Pressure) Liquid Chromatography") is an established method of separating mixtures of substances, which is widely used in biochemistry, analytical chemistry and clinical chemistry.

An HPLC apparatus consists in the simplest case of a pump with eluent reservoir containing the mobile phase, a sample application system, a separation column containing the stationary phase, and the detector. In addition, a fraction collector may also be provided, with which the individual fractions may be separately collected after separation and are thus available for further applications.

RNA analysis using ion pair reversed phase HPLC is known from A. Azarani and K. H. Hecker (Nucleic Acids Research, vol. 29, no. 2 e7). The stationary phase here consists of a non-porous alkylated polystyrenedivinylbenzene matrix. Elution proceeds with a buffer system of two eluents. Buffer A consists of an aqueous solution of 0.1 M triethylammonium acetate (TEAA), pH 7.0, and buffer B consists of an aqueous solution of 0.1 M TEAA, pH 7.0, with 25% acetonitrile. Elution was performed using the following three gradient systems: 38-40% B over 1 minute, to 60% B over 15 minutes, to 66% B over 6 minutes, to 70% B over 0.5 minutes, to 100% B over 0.5 minute, holding at 100% B for 1 minute, to 38% over 1 minute, holding at 38% B for 2 minutes. Alternatively, the following gradient program was used: 38-60% over 30 minutes, to 100% B over 2 minutes, to 38% B over 3 minutes. The following was used as a third gradient program: 38-40% B over 1 minute, to 60% B over 3 minutes, to 100% B over 1 minute, holding at 100% B over 6 minutes, to 38% B over 1 minute, holding at 38% B over 1 minute.

This HPLC method thus involved using relatively complicated and costly gradient programs. In addition, only analytical quantities of the RNA up to at most 1000 ng (1 µg or 0.001 mg) can be separated and analysed with this method.

The object of the present invention is here to improve a method of this type to the effect that it no longer exhibits the disadvantages of the prior art.

This is achieved according to the invention by a method for purifying RNA on a preparative scale, which is distinguished in that the RNA is purified by means of HPLC using a porous reversed phase as stationary phase. In the method according to the invention a significant factor is therefore that a porous reversed phase is used.

In the context of the present invention, the term "by means of HPLC" shall include various HPLC methods as well as low or normal pressure liquid chromatography methods, which may be used to carry out the inventive method. These may include reversed phase HPLC (RP-HPLC), chromatography, size exclusion chromatography, gel filtration, affinity chromatography, hydrophobic interaction chromatography or ion pair chromatography, whereby reversed phase HPLC is preferred. Without going into details, reversed phase HPLC consists of a non-polar stationary phase and a moderately polar mobile phase. One common stationary phase is e.g. a silica which has been treated with e.g. $RMe_2SiCl$, where R is a straight chain alkyl group such as $C_{18}H_{37}$ or $C_8H_{17}$. The retention time is therefore longer for molecules which are more non-polar in nature, allowing polar molecules to elute more readily. Retention time is increased by the addition of polar solvent to the mobile phase and decreased by the addition of more hydrophobic solvent.

However, the various techniques mentioned above operate on the principle of hydrophobic interactions which result from repulsive forces between a relatively polar solvent, the relatively non-polar analyte, and the non-polar stationary phase (reversed phase principle). The driving force in the binding of the analyte (the RNA molecule) to the stationary phase is the decrease in the area of the non-polar segment of the analyte molecule exposed to the solvent. This hydrophobic effect is dominated by the decrease in free energy from entropy associated with the minimization of the ordered molecule-polar solvent interface. The hydrophobic effect is decreased by adding more non-polar solvent into the mobile phase. This shifts the partition coefficient such that the analyte spends some portion of time moving down the column in the mobile phase, eventually eluting from the column.

The characteristics of the specific RNA molecule as an analyte may play an important role in its retention characteristics. In general, an analyte having more apolar functional groups results in a longer retention time because it increases the molecule's hydrophobicity. Very large molecules, however, can result in incomplete interaction between the large analyte surface and the alkyl chain. Retention time increases with hydrophobic surface area which is roughly inversely proportional to solute size. Branched chain compounds elute more rapidly than their corresponding isomers because the overall surface area is decreased.

Aside from mobile phase hydrophobicity, other mobile phase modifiers can—according to the invention—affect analyte (RNA molecule) retention. For example, the addition of inorganic salts may be considered to cause a linear increase in the surface tension of aqueous solutions, and because the entropy of the analyte-solvent interface is controlled by surface tension, the addition of salts tend to increase the retention time. Another important component, which may be used according to the invention is pH, since this can change the hydrophobicity of the analyte. For this reason, a buffering agent, such as sodium phosphate or other common buffering agents, may be used to control the pH. An organic acid, such as formic acid or most commonly trifluoroacetic acid, may be added to mobile phase. The above modifications may serve multiple purposes: They control pH, neutralize the charge on any residual exposed material on the stationary phase and act as ion pairing agents to neutralize charge on the analyte. The effect varies depending on use but generally improve the chromatography.

For the purposes of the present invention, the term "purification" is understood to mean that the desired RNA in a sample is separated and/or isolated from the impurities present therein. Thus, after HPLC purification the RNA is present in a purer form than in the originally introduced RNA-containing sample prior to HPLC purification. Undesired constituents of RNA-containing samples which therefore need to be separated may in particular be degraded fragments or fragments which have arisen as a result of premature termination of transcription, or also excessively long transcripts if plasmids are not completely linearised. In addition, impurities, such as enzymes, for example RNases and polymerases, and nucleotides may be separated.

Using the method according to the invention, RNA is purified which has a higher purity after purification than the starting material. It is desirable in this respect for the degree of purity to be as close as possible to 100%. A degree of purity of more than 70%, in particular 80%, very particularly 90% and most favourably 99% or more may be achieved in this way.

The method according to the invention results in preparative RNA purification. This differs from an analytical HPLC method, which is described in the above prior art (Azarani & Hecker). In an analytical HPLC method, a distinctly smaller quantity is introduced and separated than in a preparative HPLC method. In the method discussed in the prior art, quantities of 8 ng to 1000 ng were introduced. In contrast, a preparative HPLC method should be understood to mean an HPLC method in which relatively large quantities of RNA are purified. Such relatively large quantities are for example quantities of 0.5 mg or more, in particular 1.0 mg to 1000 mg or more, very particularly approximately 1.5 mg or more, upscaling even to the kg range being possible. The above statements are therefore to be understood to mean that these quantities relate to a single HPLC run. If a plurality of HPLC runs are performed, the quantity increases in direct proportion to the number of HPLC runs.

The method according to the invention, in particular the preferred embodiments described in detail hereinafter, exhibits a series of advantages: using the method according to the invention substantially larger quantities of RNA may be separated than is possible with the method known from the prior art. Using the method according to the invention, these relatively high quantities are obtained with a high degree of purity. Separation of degraded fragments or excessively long fragments or of fragments which have arisen as a result of premature termination of transcription is possible. In addition, good separation of further impurities present in RNA samples, such as enzymes, for example RNases and polymerases, and nucleotides is possible. These relatively large quantities of RNA may be recovered within minutes, even from samples having a very high level of contamination with impurities. RNA recovery proceeds reliably, i.e. high purity RNA is recovered with great reliability.

In the method according to the invention, a high level of resolution may be achieved. The method according to the invention may additionally easily be operated automatically. It is thus most suitable for routine purification of RNA on a preparative scale. RNA is stable under the conditions of the method according to the invention, i.e. degradation during HPLC purification into RNA fragments and thus the occurrence of new impurities and a reduction in the yield of desired RNA during HPLC purification is avoided. The method according to the invention may thus be performed in a simple, rapid, inexpensive manner, accurately and with reliable results. Isolation of RNA after HPLC separation may proceed simply with a fraction collector, i.e. the recovery of RNA may be achieved very simply, it being possible for direct further processing of the RNA likewise to take place. Detection may finally be performed very sensitively.

The "RNA" which is to be purified with the method according to the invention is ribonucleic acid of any type. The RNA is particularly preferably selected from tRNA, rRNA, mRNA or whole-cell RNA. In addition, the RNA may also comprise aptamers and ribozymes. The RNA to be isolated may be single-stranded or double-stranded. Single-stranded RNA may optionally form secondary structures by refolding, the RNA to be separated typically being single-stranded. The RNA may be unlabelled or also labelled (with a fluorescent label or a radiolabel or an antibody epitope). One example of a labelled RNA is digoxigenin-labelled β-actin RNA.

The RNA to be purified may be native or non-native RNA. Native RNA is preferably used, which is prepared using a for example cellular or in vitro expression system. The RNA is then isolated and the isolate purified using the method according to the invention. Optionally, chemically synthesised RNA may also be purified using the method according to the invention. In any event, the RNA may also contain non-native nucleotides, wherein the chemical modifications may be present in the backbone of the RNA, for example phosphorthioate, in the structure of the nucleotide base, for example hypoxanthine, dihydrouracil, pseudouracil, 2-thiouracil, 4-thiouracil, 5-aminouracil, 5-(C1-C6)-alkyluracil, 5-(C2-C6)-alkenyluracil, 5-(C2-C6)-alkynyluracil, 5-(hydroxymethyl)uracil, 5-chlorouracil, 5-fluorouracil, 5-bromouracil, 5-hydroxycytosine, 5-(C1-C6)-alkylcytosine, 5-(C2-C6)-alkenylcytosine, 5-(C2-C6)-alkynylcytosine, 5-chlorocytosine, 5-fluorocytosine, 5-bromocytosine, N<2>-dimethylguanine, 2,4-diaminopurine, 8-azapurine, a substituted 7 deazapurine, preferably 7-deaza-7-substituted and/or 7-deaza-8-substituted purine, 5-hydroxymethylcytosine, N4-alkylcytosine, for example N4-ethylcytosine, 5-hydroxydeoxycytidine, 5-hydroxymethyldeoxycytidine, N4-alkyldeoxycytidine, for example N4-ethyldeoxycytidine, 6-thiodeoxyguanosine, and deoxyribonucleotides of nitropyrrole, C5-propynylpyrimidines, and diaminopurine, for example 2,6-diaminopurine, inosine, 5-methylcytosine, 2-aminopurine, 2-amino-6-chloropurine, or also in the sugar residue. Further examples of modified nucleotides are 2-amino-6-chloropurine-riboside-5'-triphosphate, 2-aminoadenosine-5'-triphosphate, 2-thiocytidine-5'-triphosphate, 2-thiouridine-5'-triphosphate, 4-thiouridine-5'-triphosphate, 5-aminoallylcytidine-5'-triphosphate, 5-aminoallyluridine-5'-triphosphate, 5-bromocytidine-5'-triphosphate, 5-bromouridine-5'-triphosphate, 5-iodocytidine-5'-triphosphate, 5-iodouridine-5'-tri phosphate, 5-methylcytidine-5'-triphosphate, 5-methyluridine-5'-triphosphate, 6-azacytidine-5'-triphosphate, 6-azauridine-5'-triphosphate, 6-chloropurine-riboside-5'-triphosphate, 7-deazaadenosine-5'-triphosphate, 7-deazaguanosine-5'-tri phosphate, 8-azaadenosine-5'-triphosphate, 8-azidoadenosine-5'-triphosphate, benzimidazole-riboside-5'-triphosphate, N1-methyladenosine-5'-triphosphate, N1-methylguanosine-5'-triphosphate, N6-methyladenosine-5'-triphosphate, O6-methylguanosine-5'-triphosphate, pseudouridine-5'-tri phosphate, puromycine-5'-triphosphate, xanthosine-5'-tri phosphate.

In a preferred embodiment of the method according to the invention, the RNA to be separated has a size of up to about 15000 nucleotides (as single stranded RNA molecule) or base pairs (as double stranded RNA molecule), in particular 100 to 10000, more preferably 500 to 10000 nucleotides or base pairs, even more preferably 800 to 5000 nucleotides or base pairs and even more preferably 800 to 2000 nucleotides or base pairs. For this size of RNA, it has proved possible to achieve very good results with regard to purification of the RNA, since the method according to the invention is particularly well suited to RNA of this size. Optionally, however, smaller RNA fragments, for example with a length of 30-1000, 50-1000 or 100-1000 or 20-200, 20-100, 20-50 or 20-30 nucleotides may also be separated in this way.

If the RNA to be separated is mRNA, this will preferably code for proteins, in particular those which have an antigen character, and for example all recombinantly produced or naturally occurring proteins, which are known to a person skilled in the art from the prior art and are used for therapeutic, diagnostic or research purposes. In particular, the antigens are then tumour antigens or antigens of pathogens, for example viral, bacterial or protozoal organisms.

Without being limited thereto, such proteins include inter alia growth hormones or growth factors, for example for promoting growth in a (transgenic) living organism such as for example TGF and the IGFs ("insulin-like growth factors"), proteins which influence metabolism and/or haematopoiesis, such as for example (alpha-1)-anti-trypsin, LDL receptor, erythropoietin (EPO), insulin, GATA-1, etc., or proteins such as for example factors VIII and XI of the blood clotting system, etc. Such proteins further include enzymes, such as for example—galactosidase (lacZ), DNA restriction enzymes (for example EcoRI, HindIII, etc.), lysozymes, etc., or proteases, such as for example papain, bromelain, keratinases, trypsin, chymotrypsin, pepsin, rennin (chymosin), suizyme, nortase, etc., and protease inhibitors (for example for the treatment of HIV infections), such as for example protease inhibitors selected from a group consisting of AG1776, amprenavir (141W94 or VX-478), atazanavir (BMS-232632), cathepsin S protease inhibitor, D1927, D9120, fosamprenavir (GW-433908 or VX-175), GS 9005, GW640385 (VX-385), HCV protease inhibitor, indinavir (MK-639), L-756 423, Levoprin-ZG, lopinavir (ABT-378), lopinavir/ritonavir (LPV ABT-378/r), MK-944A, mozenavir (DMP450), nelfinavir (AG-1343), NNRTI, P-1946, PL-100, prinomastat, ritonavir (ABT-538), RO033-4649, TMC114, saquinavir (Ro-31-8959), NRTI, tipranavir (PNU-140690), TLK 19781, TMC-114, vertex 385, VX-950. The proteins coded from the RNA separated according to the invention may likewise comprise proteins which stimulate or inhibit cell signal transmission, for example cytokines, etc. Such proteins therefore also comprise for example cytokines of class I of the cytokine family, which comprise 4 positionally conserved cysteine residues (CCCC) and one conserved sequence motif Trp-Ser-X-Trp-Ser (WSXWS), wherein X represents a non-conserved amino acid. Cytokines of class I of the cytokine family comprise the GM-CSF subfamily, for example IL-3, IL-5, GM-CSF, the IL-6 subfamily, for example IL-6, IL-11, IL-12, or the IL-2 subfamily, for example IL-2, IL-4, IL-7, IL-9, IL-15, etc., or the cytokines IL-1, IL-1, IL-10 etc. Likewise, such proteins may also comprise cytokines of the class II of the cytokine family (interferon receptor family), which likewise comprise 4 positionally conserved cysteine residues (CCCC), but no conserved sequence motif Trp-Ser-X-Trp-Ser (WSXWS). Cytokines of class II of the cytokine family include for example IFN-alpha, IFN-beta, IFN-gamma, etc. The proteins coded by the separated RNA may furthermore also include cytokines of the tumour necrosis family including for example TNF-alpha, TNF-beta, CD40 ligand, Fas ligand, etc., or cytokines of the chemokine family, in particular interferons, interleukins, colony-stimulating factors and tumour necrosis factors, and interact with G protein, for example IL-8, MIP-1, RANTES, CCR5, CXR4, etc. Such proteins may also be selected from apoptosis factors or apoptosis-related or -linked proteins, including AIF, Apaf, for example Apaf-1, Apaf-2, Apaf-3, or APO-2 (L), APO-3 (L), apopain, Bad, Bak, Bax, Bcl-2, Bcl-$x_L$, Bcl-$x_S$, bik, CAD, calpain, caspases for example caspase-1, caspase-2, caspase-3, caspase-4, caspase-5, caspase-6, caspase-7, caspase-8, caspase-9, caspase-10, caspase-11, ced-3, ced-9, c-Jun, c-Myc, crm A, cytochrome C, CdR1, DcR1, DD, DED, DISC, DNA-$PK_{CS}$, DR3, DR4, DR5, FADD/MORT-1, FAK, Fas (Fas ligand CD95/fas (receptor)), FLICE/MACH, FLIP, fodrin, fos, G-actin, Gas-2, gelsolin, granzymes A/B, ICAD, ICE, JNK, lamin A/B, MAP, MCL-1, Mdm-2, MEKK-1, MORT-1, NEDD, NF-B, NuMa, p53, PAK-2, PARP, perforin, PITSLRE, PKC, pRb, presenilin, prICE, RAIDD, Ras, RIP, sphingomyelinase, thymidine kinase from Herpes simplex, TRADD, TRAF2, TRAIL, TRAIL-R1, TRAIL-R2, TRAIL-R3, transglutaminase, etc. The proteins coded by RNA separated according to the invention may also be selected from antigens, for example from tumour-specific surface antigens (TSSA), for example 5T4alpha5 beta1 integrin, 707-AP, AFP, ART-4, B7H4, BAGE, Bcr-abl, MN/C IX-antigen, CA125, CAMEL, CAP-1, CASP-8, beta-catenin/m, CD4, CD19, CD20, CD22, CD25, CDC27/m, CD30, CD33, CD52, CD56, CD80, CDK4/m, CEA, CT, Cyp-B, DAM, EGFR, ErbB3, ELF2M, EMMPRIN, EpCam, ETV6-AML1, G250, GAGE, GnT-V, Gp100, HAGE, HER-2/new, HLA-A*0201-R170I, HPV-E7, HSP70-2M, HAST-2, hTERT (or hTRT), iCE, IGF-1R, IL-2R, IL-5, KIAA0205, LAGE, LDLR/FUT, MAGE, MART-1/melan-A, MART-2/Ski, MC1R, myosin/m, MUC1, MUM-1, -2, -3, NA88-A, PAP, proteinase-3, p190 minor bcr-abl, Pml/RAR, PRAME, PSA, PSM, PSMA, RAGE, RU1 or RU2, SAGE, SART-1 or SART-3, survivin, TEUAML1, TGF, TPI/m, TRP-1, TRP-2, TRP-2/INT2, VEGF and WT1, or from sequences, such as for example NY-Eso-1 or NY-Eso-B. Proteins which may be coded by the RNA separated according to the invention additionally also include proteins or protein sequences which exhibit sequence identity of at least 80% or 85%, preferably at least 90%, more preferably at least 95% and most preferably at least 99% to one of the above-described proteins.

The mRNA to be separated may exhibit the following modifications relative to a corresponding wild-type mRNA, which may either be present as alternatives or in combination.

On the one hand, the G/C content of the region of the modified mRNA coding for a peptide or polypeptide may be greater than the G/C content of the coding region of the wild-type mRNA coding for the peptide or polypeptide, the coded amino acid sequence being unchanged relative to the wild-type. This modification is based on the fact that the sequence order of the mRNA domain to be translated is essential for efficient mRNA translation. In this respect, the composition and sequence of the various nucleotides has an important part to play. In particular, sequences with an elevated G(guanosine)/C(cytosine) content are more stable than sequences with an elevated A(adenosine)/U(uracil) content. Thus, according to the invention, while retaining the translated amino acid sequence, the codons are varied relative to the wild-type mRNA in such a manner that they have a greater content of G/C nucleotides. Since several codons code for one and the same amino acid (degeneration of the genetic code), it is possible to determine the codons which are most favourable for stability (alternative codon usage). On the other hand it is also possible to provide a translation-optimised RNA with the method according to the invention.

In the method according to the invention, a reversed phase is used as the stationary phase for HPLC purification. For chromatography with reversed phases, a nonpolar compound serves as the stationary phases and a polar solvent, such as mixtures of water, which is generally used in the form of buffers, with e.g. acetonitrile and/or methanol, serves as the mobile phase for elution.

The material packed on the column, which is used as stationary phase, may be provided in bead form or as a polymerized "block", i.e. a block which fills a substantial part of the chromatography column. Irrespective of its precise nature, the polymeric stationary phase is porous in its nature, which means that the beads or the block are characterized by pores.

In a preferred embodiment of the method according to the invention, the porous reversed phase material is provided with a particle size of 8.0 μm to 50 μm, in particular 8.0 to 30, still more preferably 8.0 to 25 μm. The reversed phase material may be present in the form of small spheres. The method according to the invention may be performed particularly favourably with a porous reversed phase with this particle size, optionally in bead form, wherein particularly good separation results are obtained.

The reversed phase used in the method according to the invention is porous and has specific particle sizes. With stationary reversed phases which are not porous and thus differ completely with regard to particle size from the subject matter of the present invention as described for example by A. Azarani and K. H. Hecker, on the other hand, excessively high pressures are built up, such that preparative purification of the RNA is possible only with great difficulty, if at all.

In a preferred embodiment of the method according to the invention, the reversed phase has a pore size of 1000 Å to 5000 Å, in particular a pore size of 1000 Å to 4000 Å, more preferably 1500 Å to 4000 Å, 2000 Å to 4000 Å or 2500 Å to 4000 Å. Particularly preferred pore sizes for the reversed phases are 1000 Å to 2000 Å, more preferably 1000 Å to 1500 Å and most preferably 1000 Å to 1200 Å or 3500-4500 Å. With a reversed phase having these pore sizes, particularly good results are achieved with regard to purification of the RNA using the method according to the invention, in particular the elevated pressures built up in the method according to A. Azarani and K. H. Hecker are thus avoided, whereby preparative separation is made possible in a particularly favourable manner. At pore sizes of below 1000 Å separation of RNA molecules becomes poorer.

A pore size of 1000 Å to 5000 Å, in particular a pore size of 1000 Å to 4000 Å, more preferably 1500 Å to 4000 Å, 2000 Å to 4000 Å or 2500 Å to 4000 Å may be suitable to separate a RNA from other components of a mixture, the RNA having a size as mentioned above of up to about 15000 nucleotides (as single stranded RNA molecule) or base pairs (as double stranded RNA molecule), in particular 100 to 10000, more preferably 500 to 10000 nucleotides or base pairs, even more preferably 800 to 5000 nucleotides or base pairs and even more preferably 800 to 2000 nucleotides or base pairs. However, the pore size of the reversed phase may also be selected in dependence of the size of the RNA to be separated, i.e. a larger pore size may be selected, if larger RNA molecules are to be separated and smaller pore sizes may be selected, if smaller RNA molecules may be selected. This is due to the effect, that the retention of the RNA molecules and the separation not only depends on the interaction of the (reversed) phase but also on the possibility of molecules to get inside the pores of the matrix and thus provide a further retention effect. Without being limited thereto, e.g. a pore size for the reversed phase of about 2000 Å to about 5000 Å, more preferably of about 2500 to about 4000, most preferably of about 3500 to about 4500 Å, may thus be used to separate larger RNA molecules, e.g. RNA molecules of 100 to 10000, more preferably 500 to 10000 nucleotides or base pairs, even more preferably 800 to 5000 nucleotides or base pairs and even more preferably 800 to 2000 nucleotides or base pairs. Alternatively, without being limited thereto, a pore size of for the reversed phases of about 1000 Å to about 2500 Å, more preferably of about 1000 Å to about 2000 Å, and most preferably of about 1000 Å to 1200 Å may be used to separate smaller RNA molecules, e.g. RNA molecules of about 30-1000, 50-1000 or 100-1000 or 20-200, 20-100, 20-50 or 20-30 nucleotides may also be separated in this way.

In general, any material known to be used as reverse phase stationary phase, in particular any polymeric material may be used for the inventive method, if that material can be provided in porous form. The stationary phase may be composed of organic and/or inorganic material. Examples for polymers to be used for the present invention are (non-alkylated) polystyrenes, (non-alkylated) polystyrenedivinylbenzenes, silica gel, silica gel modified with non-polar residues, particularly silica gel modified with alkyl containing residues, more preferably with butyl-, octyl and/or octadecyl containing residues, silica gel modified with phenylic residues, polymethacrylates, etc. or other materials suitable e.g. for gelchromatographie or other chromatographic methods as mentioned above, such as dextran, including e.g. Sephadex® and Sephacryl® materials, agarose, dextran/agarose mixtures, polyacrylamide, etc.

In a particularly preferred embodiment, the material for the reversed phase is a porous polystyrene polymer, a (non-alkylated) (porous) polystyrenedivinylbenzene polymer, porous silica gel, porous silica gel modified with non-polar residues, particularly porous silica gel modified with alkyl containing residues, more preferably with butyl-, octyl and/or octadecyl containing residues, porous silica gel modified with phenylic residues, porous polymethacrylates, wherein in particular a porous polystyrene polymer or a non-alkylated (porous) polystyrenedivinylbenzene may be used. Stationary phases with polystyrenedivinylbenzene are known per se. The per se known polystyrenedivinyl-benzenes already used for HPLC methods, which are commercially obtainable, may be used for the method according to the invention.

A non-alkylated porous polystyrenedivinylbenzene which is very particularly preferred for the method according to the invention is one which, without being limited thereto, may have in particular a particle size of 8.0±1.5 μm, in particular 8.0±0.5 μm, and a pore size of 1000-1500 Å, in particular 1000-1200 Å or 3500-4500 Å. With this material for the reversed phases, the above-described advantages of the method according to the invention may be achieved in a particularly favourable manner.

This stationary phase described in greater detail above is conventionally located in a column. V2A steel is conventionally used as the material for the column, but other materials may also be used for the column provided they are suitable for the conditions prevailing during HPLC. Conventionally the column is straight. It is favourable for the HPLC column to have a length of 5 cm to 100 cm and a diameter of 4 mm to 25 mm. Columns used for the method according to the invention may in particular have the following dimensions: 50 mm long and 7.5 mm in diameter or 50 mm long and 4.6 mm in diameter, or 50 mm long and 10 mm in diameter or any other dimension with regard to length and diameter, which is suitable for preparative recovery of RNA, even lengths of several meters and also larger diameters being feasible in the case of upscaling. The dimensions are here geared towards what is technically possible with liquid chromatography.

In a preferred embodiment, the method according to the invention is performed as an ion pair method, wherein an ion with a lipophilic residue and positive charge is added to the mobile phase as counterion for the negatively charged RNA. In this way, an ion pair with lipophilic character is obtained, which is slowed down by the nonpolar stationary phase of the reversed phase system. In practice, the precise conditions for the ion pair method have to be empirically worked out for each specific separation problem. The size of the counterion, its concentration and the pH value of the solution contribute greatly to the separation result. This means that the empirically established conditions of an ion pair method cannot be straightforwardly applied to a different separation problem. If, for example, an ion pair method is known from the prior art, this does not mean that the same conditions may inevitably also be applied to the separation problem underlying the present invention, even if ultimately the same or similar conditions may in fact prove to be favourable. Alkylammonium salts, such as triethylammonium acetate, and/or tetraalkylammonium compounds, such as tetrabutylammonium, are favourably added in the method according to the invention.

Preferably, 0.1 M triethylammonium acetate is added and the pH value is adjusted to about 7. This buffer for the ion pair method solves the separation problem underlying the present invention, i.e. the purification of RNA on a preparative scale, in a particularly favourable manner. The following may be considered as further buffer solutions: trifluoroacetic acid, acetic acid, formic acid, acetate buffer, phosphate buffer, tetrabutylammonium bisulfate, tetrabutylammonium bromide and tetrabutylammonium chloride.

Selection of the mobile phase depends on the type of separation desired. This means that the mobile phase established for a specific separation, as may be known for example from the prior art, cannot be straightforwardly applied to a different separation problem with a sufficient prospect of success. For each separation problem, the ideal elution conditions, in particular the mobile phase used, have to be determined by empirical testing.

In a preferred embodiment of the HPLC method according to the invention, a mixture of an aqueous solvent and an organic solvent is used as the mobile phase for eluting the RNA. It is favourable for a buffer to be used as the aqueous solvent which has in particular a pH of 6.0-8.0, for example of about 7, for example. 7.0; preferably the buffer is triethylammonium acetate, particularly preferably a 0.02 M to 0.5 M, in particular 0.08 M to 0.12 M, very particularly an about 0.1 M triethylammonium acetate buffer, which, as described above, also acts as a counterion to the RNA in the ion pair method.

In a preferred embodiment, the organic solvent which is used in the mobile phase is acetonitrile, methanol, ethanol, 1-propanol, 2-propanol and acetone or a mixture thereof, very particularly preferably acetonitrile. With these organic solvents, in particular acetonitrile, purification of the RNA proceeds in particularly favourable manner with the method according to the invention.

In a particularly preferred embodiment of the method according to the invention, the mobile phase is a mixture of 0.1 M triethylammonium acetate, pH 7, and acetonitrile.

It has proven particularly favourable for the method according to the invention for the mobile phase to contain 5.0 vol. % to 25.0 vol. % organic solvent, relative to the mobile phase, and for this to be made up to 100 vol. % with the aqueous solvent. Typically, in the event of gradient separation, the proportion of organic solvent is increased, in particular by at least 10%, more preferably by at least 50% and most preferably by at least 100%, optionally by at least 200%, relative to the initial vol. % in the mobile phase. In a preferred embodiment, in the method according to the invention the proportion of organic solvent in the mobile phase amounts in the course of HPLC separation to 3 to 9, preferably 4 to 7.5, in particular 5.0 vol. %, in each case relative to the mobile phase. More preferably, the proportion of organic solvent in the mobile phase is increased in the course of HPLC separation from 3 to 9, in particular 5.0 vol. % to up to 20.0 vol. %, in each case relative to the mobile phase. Still more preferably, the method is performed in such a way that the proportion of organic solvent in the mobile phase is increased in the course of HPLC separation from 6.5 to 8.5, in particular 7.5 vol. %, to up to 17.5 vol. %, in each case relative to the mobile phase.

It has proven even more particularly favourable for the method according to the invention for the mobile phase to contain 7.5 vol. % to 17.5 vol. % organic solvent, relative to the mobile phase, and for this to be made up to 100 vol. % with the aqueous buffered solvent.

In the case of the method according to the invention elution may proceed isocratically or by means of gradient separation. In isocratic separation, elution of the RNA proceeds with a single eluent or a constant mixture of a plurality of eluents, wherein the solvents described above in detail may be used as eluent.

In a preferred embodiment of the method according to the invention, gradient separation is performed. In this respect, the composition of the eluent is varied by means of a gradient program. The equipment necessary for gradient separation is known to a person skilled in the art. Gradient elution may here proceed either on the low pressure side by mixing chambers or on the high pressure side by further pumps.

Preferably, in the method according to the invention, the proportion of organic solvent, as described above, is increased relative to the aqueous solvent during gradient separation. The above-described agents may here be used as the aqueous solvent and the likewise above-described agents may be used as the organic solvent.

For example, the proportion of organic solvent in the mobile phase may be increased in the course of HPLC separation from 5.0 vol. % to 20.0 vol. %, in each case relative to the mobile phase. In particular, the proportion of organic solvent in the mobile phase may be increased in the course of HPLC separation from 7.5 vol. % to 17.5 vol. %, in particular 9.5 to 14.5 vol. %, in each case relative to the mobile phase.

The following gradient program has proven particularly favourable for the purification of RNA with the method according to the invention:
Eluent A: 0.1 M triethylammonium acetate, pH 7
Eluent B: 0.1 M triethylammonium acetate, pH 7, with 25 vol. % acetonitrile
Eluent composition:
   start: 62% A and 38% B (1st to 3rd minute)
   increase to 58% B (1.67% increase in B per minute), (3rd-15th minute)
   100% B (15th to 20th minute)
Another example of a gradient program is described below, the same eluent A and B being used:
Eluent composition:
   starting level: 62% A and 38% B (1st-3rd min)
   separation range I: gradient 38%-49.5% B (5.75% increase in B/min) (3rd-5th min)
   separation range II: gradient 49.5%-57% B (0.83% increase in B/min) (5th-14th min)
   rinsing range: 100% B (15th-20th min)

So that the column is not soiled or clogged and detection is not disrupted, it is favourable to use purified solvent for HPLC. Such purified solvents are commercially obtainable. They may additionally also be filtered with a 1 to 5 µm microfilter, which is generally mounted in the system upstream of the pump. It is additionally favourable for all the solvents to be degassed prior to use, since otherwise gas bubbles occur in most pumps. If air bubbles occur in the solvent, this may interfere not only with separation but also with the continuous monitoring of outflow in the detector. The solvents may be degassed by heating, by vigorous stirring with a magnetic stirrer, by brief evacuation, by ultrasonication or by passing a small stream of helium through the solvent storage vessel.

The flow rate of the eluent is so selected that good separation of the RNA from the other constituents contained in the sample to be investigated takes place. The eluent flow rate selected for the method according to the invention may amount to from 1 ml/min to several litres per minute (in the case of upscaling), in particular about 1 to 1000 ml/min, more preferably 5 ml to 500 ml/min, even more preferably more than 100 ml/min, depending on the type and scope of the upscaling. This flow rate may be established and regulated by the pump.

Detection proceeds favourably with a UV detector at 254 nm, wherein a reference measurement may be made at 600 nm. However, any other detection method may alternatively be used, with which the RNA described above in greater detail may be detected in satisfactory and reliable manner.

For preparative purification of the RNA with the method according to the invention, it is advisable to collect the RNA-containing eluted solvent quantities. In this respect, it is favourable to carry out this collection in such a way that the eluted solvent is collected in individual separated fractions. This may take place for example with a fraction collector. In this way, the high-purity RNA-containing fractions may be separated from other RNA-containing fractions which still contain undesired impurities, albeit in very small quantities. The individual fractions may be collected for example over 1 minute.

The method according to the invention is favourably performed under completely denaturing conditions. This may proceed for example in that sample application takes place at a temperature of 4-12° C., the HPLC method otherwise proceeding at a higher temperature, preferably at 70° C. or more, particularly preferably at 75° C. or more, in particular up to 82° C., and very particularly preferably at about 78° C. Heating is typically important for denaturing the RNA, whereby better separation is ultimately achieved. Resolution falls at lower temperatures, i.e. separation of the RNA from the impurities decreases.

Sample application may be performed with two methods, stop-flow injection or loop injection. For stop-flow injection a microsyringe is used which is able to withstand the high pressure applied in HPLC. The sample is injected through a septum in an inlet valve either directly onto the column packing or onto a small drop of inert material immediately over the packing. The system may in this case be under elevated pressure, or the pump may be turned off prior to injection, which is then performed when the pressure has fallen to close to the normal value. In the case of loop injection, a loop injector is used to introduce the sample. This consists of a tubular loop, into which the sample is inserted. By means of a suitable rotary valve, the stationary phase is then conveyed out of the pump through the loop, whose outlet leads directly into the column. The sample is entrained in this way by the stationary phase into the column, without solvent flow to the pump being interrupted.

The present invention further provides the use of a porous reversed phase in the above-described HPLC method according to the invention.

In a preferred embodiment of the method according to the invention, the porous reversed phase has a particle size of 8.0 µm to 50 µm, in particular 8.0 to 30, still more preferably 8.0 to 25 µm. The reversed phase may be present in bead form. The method according to the invention may be performed particularly favourably with a porous reversed phase with this particle size and/or in the form of beads, wherein particularly good separation results are obtained.

The reversed phase used for the use according to the invention is porous, since with stationary reversed phases, which are not porous, and thus differ completely with regard to particle size from the subject matter of the present invention, as described for example by A. Azarani and K. H. Hecker, excessively high pressures are built up, such that preparative purification of the RNA by means of HPLC is possible only with great difficulty, if at all.

In one preferred embodiment of the use according to the invention, the reversed phase has a pore size of 1000 Å to 5000 Å, in particular a pore size of 1000 Å to 4000 Å, or the above-stated preferred values. Particularly preferred pore sizes for the reversed phases are 1000-1200 Å and 3500-4500 Å. With a reversed phase having these pore sizes, particularly good results are achieved with regard to purification of the RNA using the method according to the invention, in particular the elevated pressures built up in the method according to A. Azarani and K. H. Hecker are thus avoided, whereby preparative separation is made possible in a particularly favourable manner. At pore sizes of below 1000 Å, separation of the RNA becomes poorer, for which reason such particle sizes are less preferable. However, the pore size may be selected in dependence of the RNA size to be separated, as mentioned above.

In a particularly preferred embodiment of the use according to the invention, the material for the reversed phase is a polystyrenedivinylbenzene, wherein in particular non-alkylated polystyrenedivinylbenzene may be used. Stationary phases with polystyrenedivinylbenzene are known per se. The per se known polystyrenedivinylbenzenes already used for HPLC methods, which are commercially obtainable, may be used for the method according to the invention.

A non-alkylated porous polystyrenedivinylbenzene which is very particularly preferred for the use according to the invention is one which has in particular a particle size of 8.0±1.5 µm, in particular 8.0±0.5 µm, and a pore size of 1000- or 4000 Å. With this material for the reversed phase, the advantages described below may be achieved in a particularly favourable manner.

For the use according to the invention, this stationary phase described in greater detail above is located in a column. V2A steel is conventionally used as the material for the column, but other materials may also be used for the column provided they are suitable for the conditions prevailing during HPLC recovery. Conventionally the column is straight. It is favourable for the HPLC column to have a length of 5 cm to 100 cm and a diameter of 4 mm to 25 mm. Columns used for the method according to the invention may in particular have the following dimensions: 50 mm long and 7.5 mm in diameter or 50 mm long and 4.6 mm in diameter, or 50 mm long and 10 mm in diameter or any other dimension with regard to length and diameter, which is suitable for preparative purification of RNA by means of HPLC, even lengths of several meters and also larger diameters being feasible in the case of upscaling. The dimensions are here geared towards what is technically possible with liquid chromatography.

Further conditions for the use according to the invention have already been described above in connection with the method according to the invention, such that reference is made thereto to avoid unnecessary repetition.

The use according to the invention, in particular the preferred embodiments described in detail hereinafter, exhibits a series of advantages: in the context of the use according to the invention, substantially larger quantities of RNA may be separated than is possible with the methods known from the prior art. The use according to the invention enables these higher quantities to be obtained with a high degree of purity. Separation of degraded fragments or of relatively long fragments or of fragments which have arisen as a result of premature termination of transcription is possible. In addition, good separation of further impurities present in RNA samples, such as enzymes, for example RNases or polymerases, and nucleotides is possible. These relatively large quantities of RNA may be recovered within minutes, even from samples having a very high level of contamination with impurities. RNA recovery proceeds reliably, i.e. high purity RNA is recovered with great reliability. The use according to the invention enables high resolution to be achieved. The use according to the invention may easily be operated automatically. It is thus most suitable for routine purification of RNA on a preparative scale. RNA is stable under the conditions of the HPLC separation method, i.e. degradation into RNA fragments and thus the occurrence of new impurities or a reduction in the yield of pure RNA during HPLC purification is avoided. The use according to the invention may thus be performed in a simple, rapid, inexpensive manner, accurately and with reliable results. Isolation of RNA after HPLC separation may proceed simply with a fraction collector, i.e. the recovery of RNA may be achieved very simply, direct further processing of the RNA likewise being possible. Detection may proceed very sensitively.

The invention is explained in greater detail below with reference to the Figures and an exemplary embodiment, without being limited thereto.

FIGURES

FIG. 9 shows the sequence of the wild-type of luciferase, specifically the mRNA sequence, which was used for the exemplary embodiments.

Figure 10:
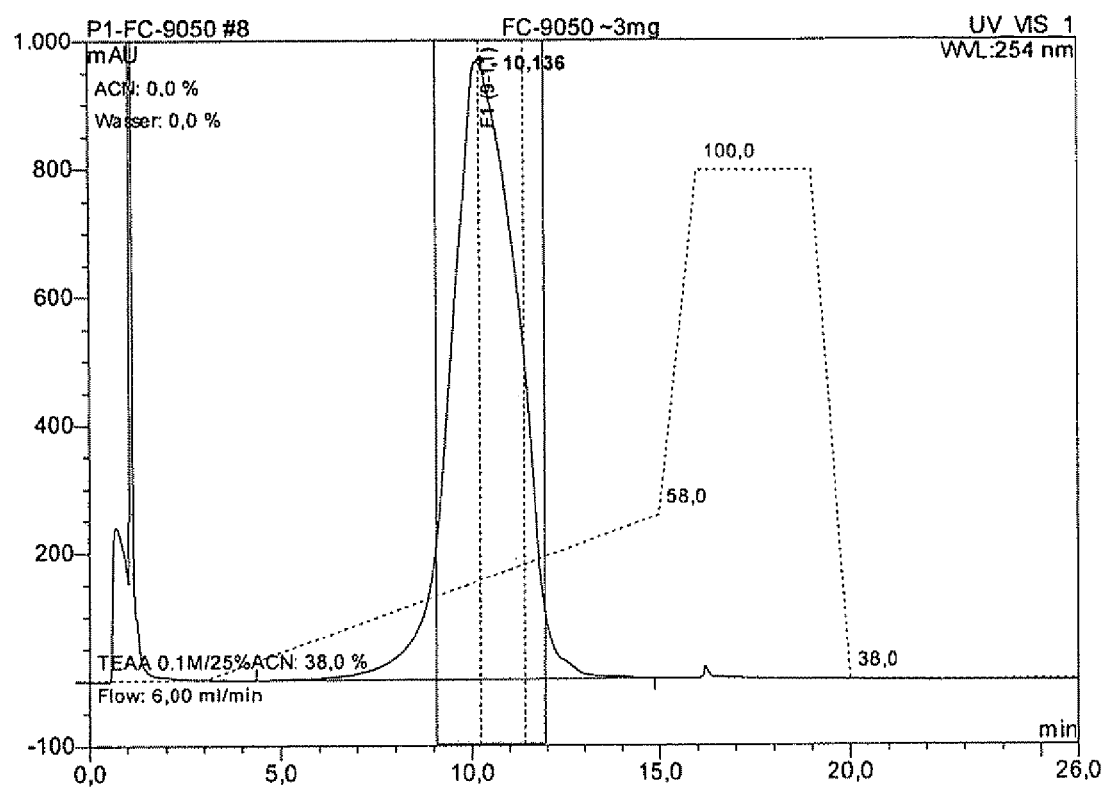
Figure 11:
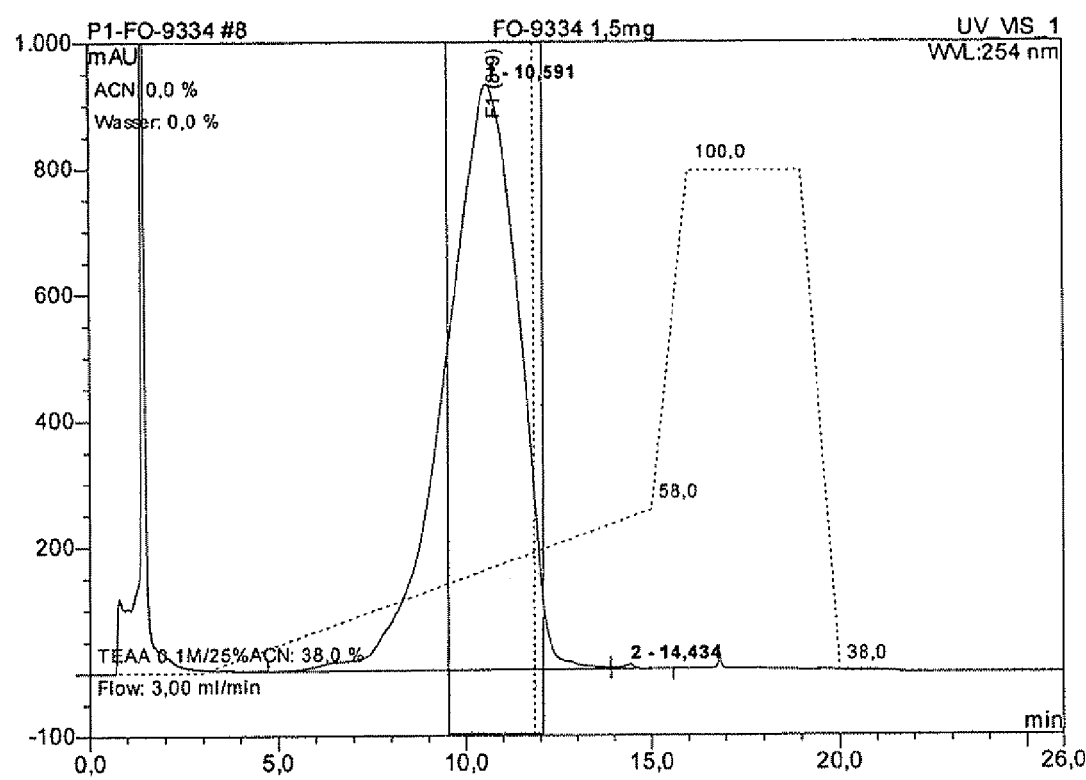
Figure 12:
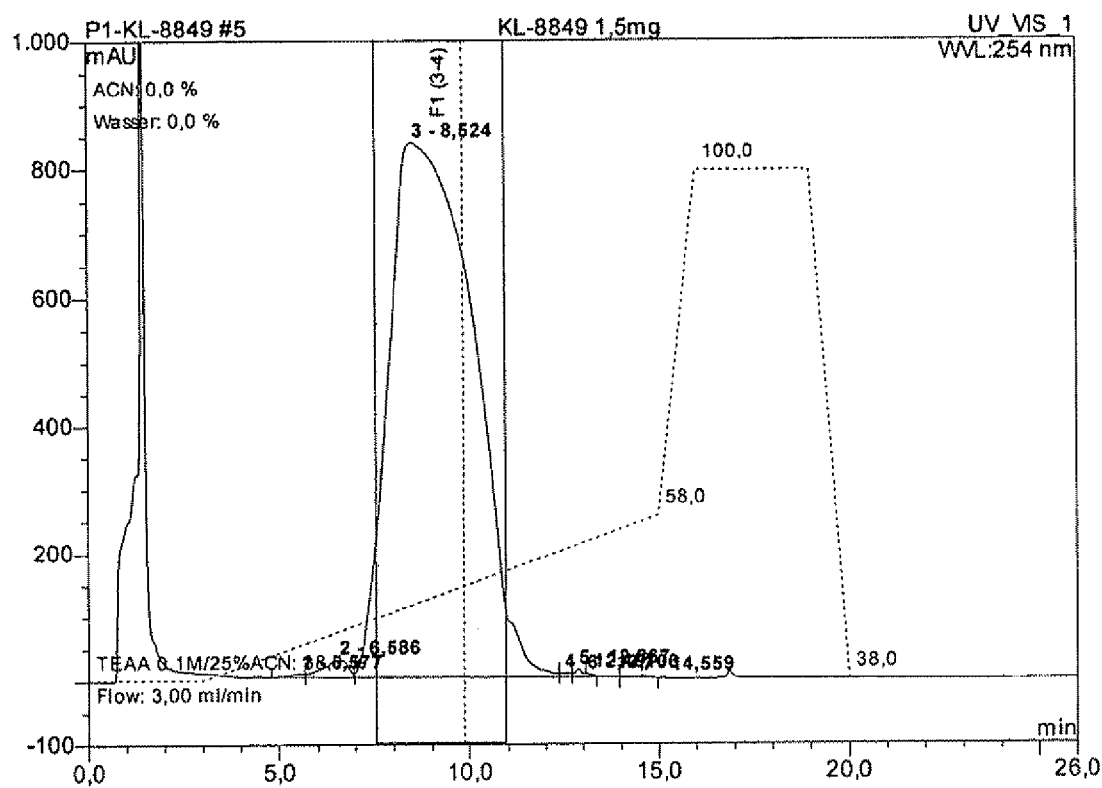
Figure 13:
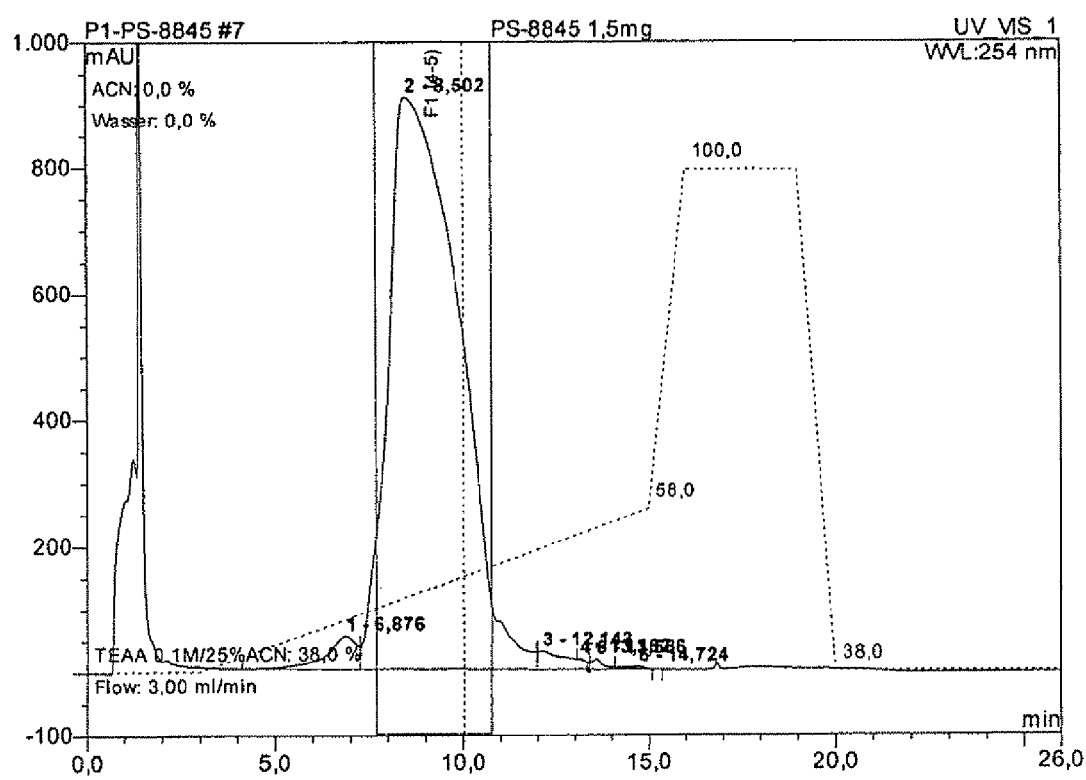
Figure 14:
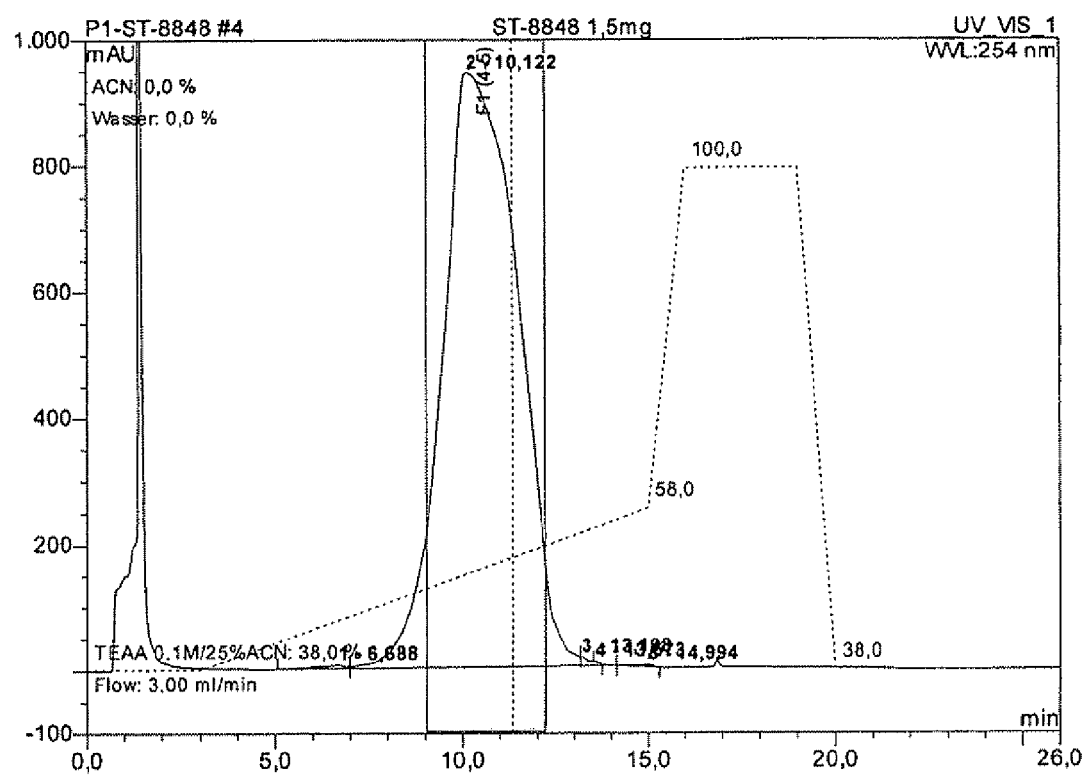
Figure 15:
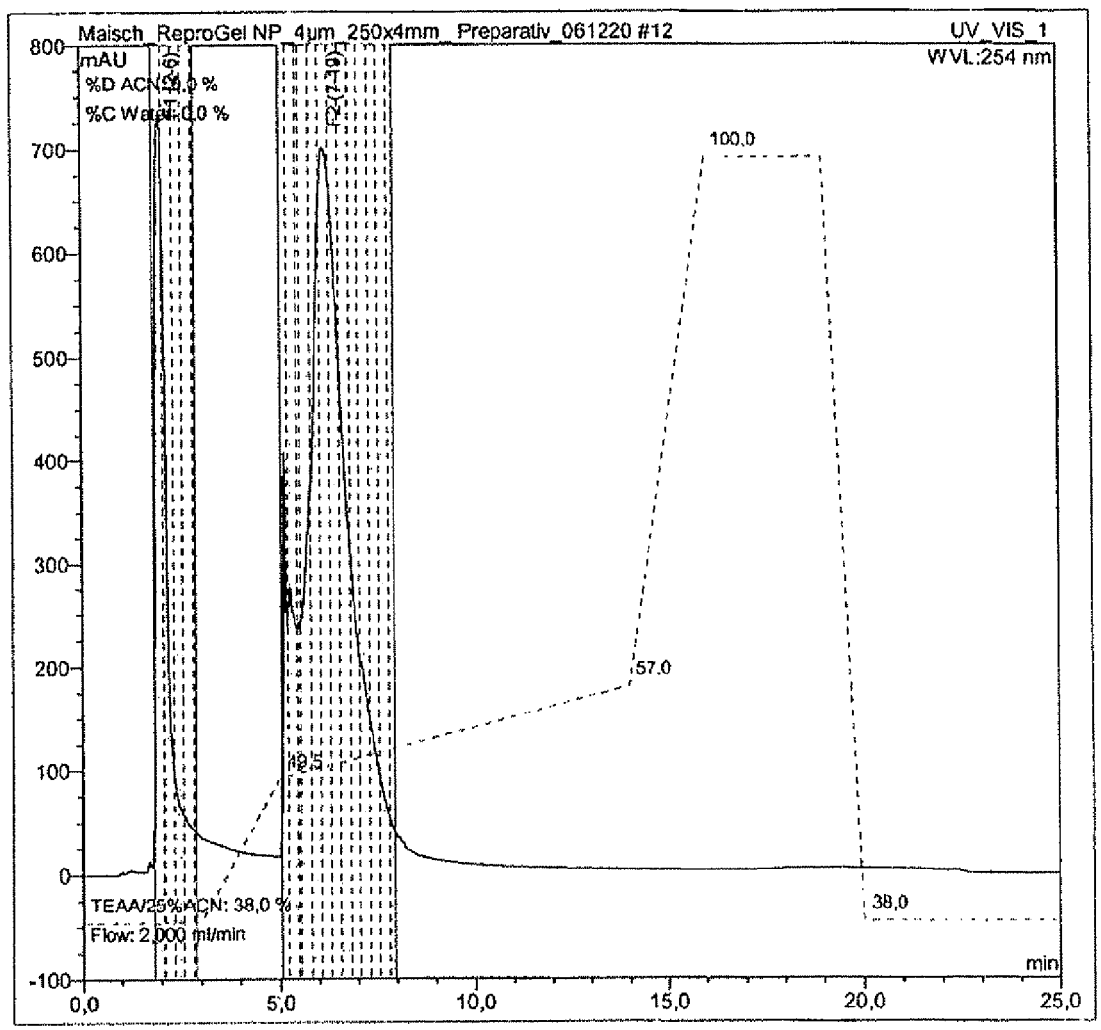
Figure 16:
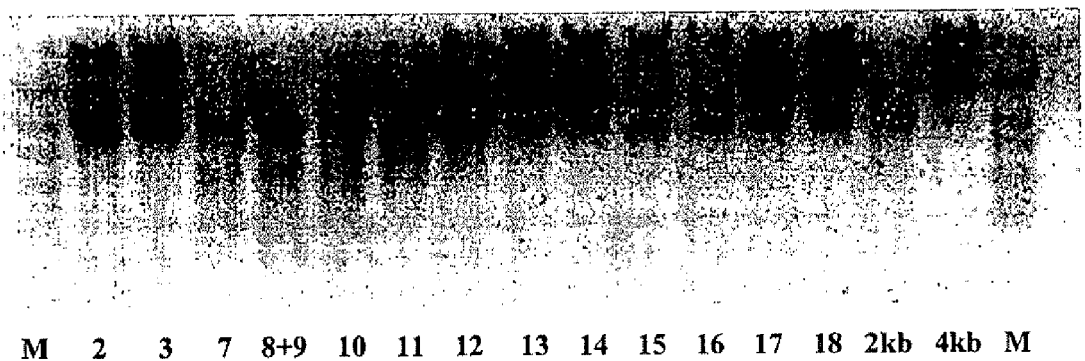

FIG. 10 shows a chromatogram of a separation of 3 mg of a Flic(GC) RNA preparation (FC-9050) with a stationary matrix, which has a pore size of 4000 Å, FIG. 11 shows a chromatogram of a separation of 1.5 mg of a FOLH1(GC) RNA preparation (FO-9334) with a stationary matrix, which has a pore size of 4000 Å, FIG. 12 shows a chromatogram of a separation of 1.5 mg of a KLK3(GC) RNA preparation (KL-8849) with a stationary matrix, which has a pore size of 4000 Å, FIG. 13 shows a chromatogram of a separation of 1.5 mg of a PSCA(GC) RNA preparation (PS-8845) with a stationary matrix, which has a pore size of 4000 Å, FIG. 14 shows a chromatogram of a separation of 1.5 mg of a STEAP(GC) RNA preparation (ST-8848) with a stationary matrix, which has a pore size of 4000 Å, FIG. 15 shows a chromatogram of a separation of a mixture of a 2 kb RNA (200 µg) and a 4 kb RNA (200 µg) with a non-porous stationary matrix;

FIG. 16 shows an agarose gel analysis corresponding to the chromatogram according to FIG. 15, which shows a separation of a mixture of a 2 kb RNA (200 µg) and a 4 kb RNA (200 µg) with a non-porous stationary matrix;

EXAMPLE 1

Purification of 1.5 Mg of Luciferase mRNA by Means of the HPLC Method According to the Invention Luciferase mRNA having a size of 1825 base pairs was used for separation. A porous, non-alkylated polystyrene/divinylbenzene (polystyrenedivinylbenzene) matrix (conventional commercial product from Polymer Laboratories) was used as the stationary phase. It had a particle size of 8 µm and a pore size of 4000 Å. The column used was 5.0 cm long and had a diameter of 7.5 mm. The sampler temperature was 12° C., the temperature for the HPLC separation, in particular of the separation column, was 78° C., i.e. operations were carried out under completely denaturing conditions.
Separation Proceeded Via a Gradient Program:
    Eluent A: 0.1 M triethylammonium acetate, pH 7
    Eluent B: 0.1 M triethylammonium acetate, pH 7, with 25 vol. % acetonitrile
    Eluent composition:
        start: 62% A and 38% B (1st to 3rd minute) increase to 58% B (1.67% increase in B per minute), (3rd-15th minute)
        100% B (15th to 20th minute)
    Detection proceeded with a UV detector at 254 nm with a reference measurement at 600 nm. Flow rate was 3 ml/min.

Figure 1:
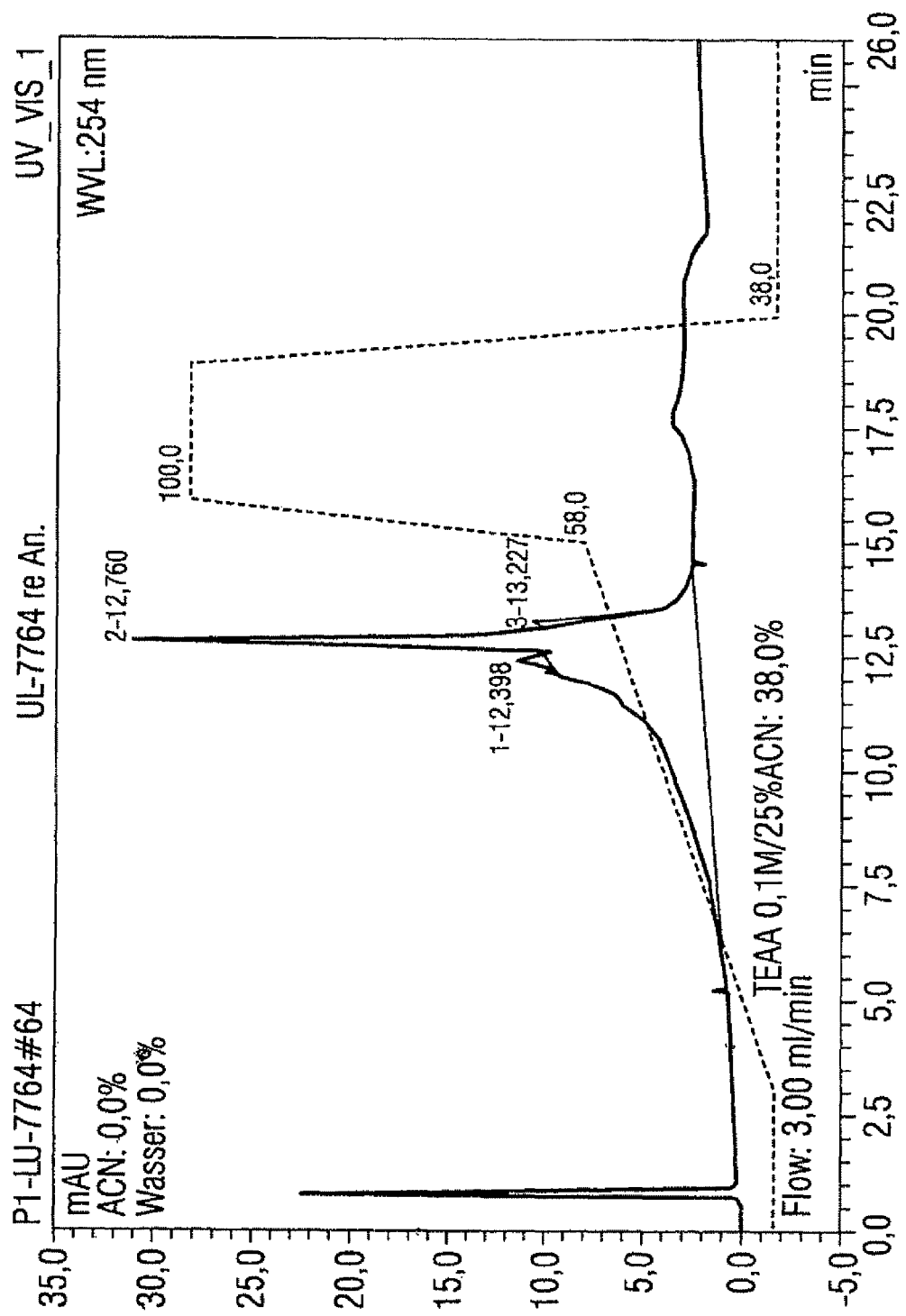
FIG. 1 shows a chromatogram of a separation of 10 µg of luciferase-mRNA (analytical)

In order to show the impurities in the luciferase mRNA, first of all an analytical separation was performed, in which only 10 µg of the luciferase mRNA was applied to the column. The result of this analytical HPLC separation is shown in FIG. 1 (the gradient is shown with broken lines in the chromatogram). As may clearly be seen, in addition to the desired mRNA of luciferase (retention time 12.760 minutes), impurities are still present (retention times of 12.398 minutes and 13.227 minutes), which flank the luciferase mRNA peak.

The purpose of purifying the luciferase mRNA on a preparative scale is to remove these undesired impurities.

Figure 2:
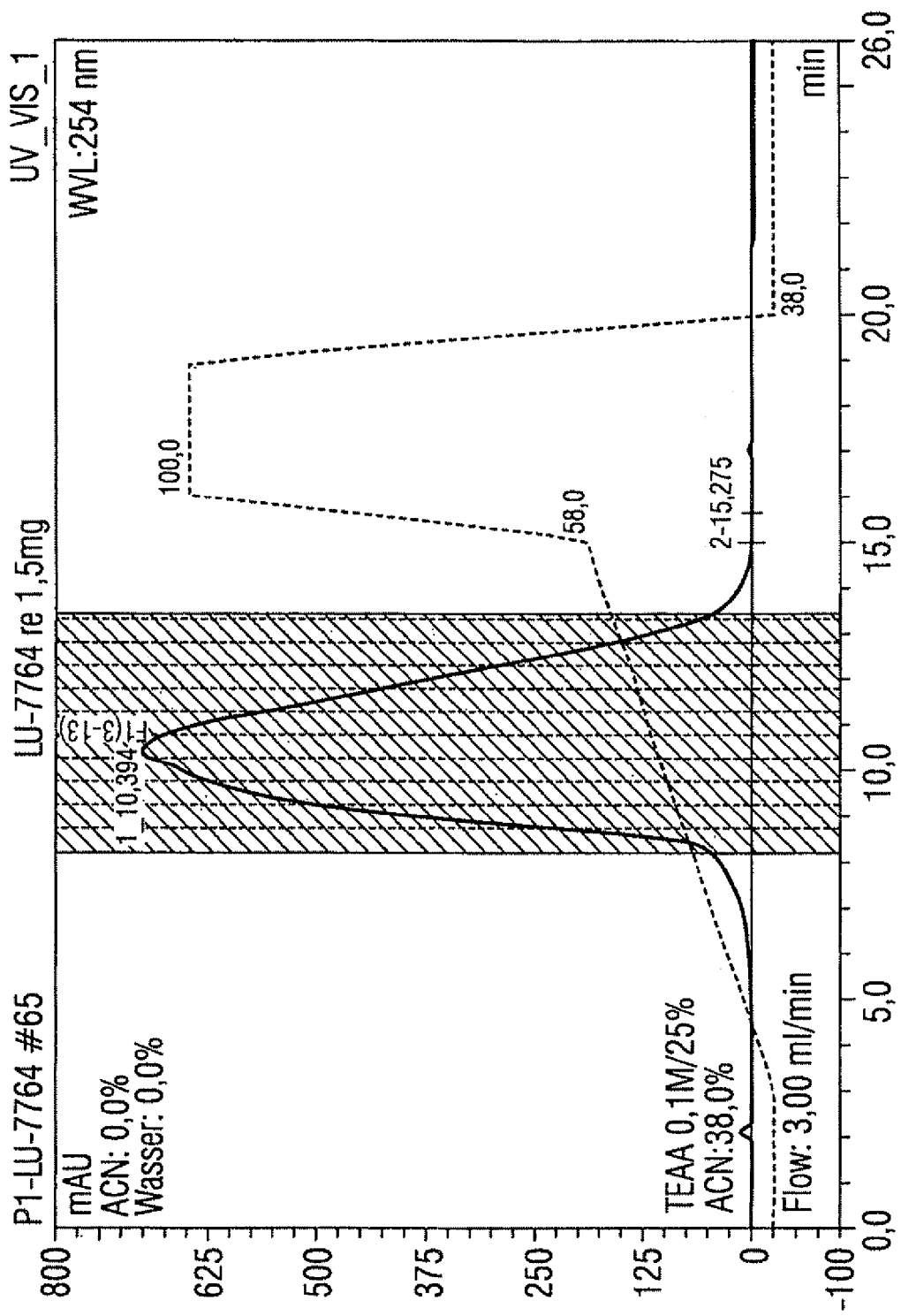
FIG. 2 shows a chromatogram of a separation of 1.5 µg of luciferase-mRNA (preparative)
Figure 3:
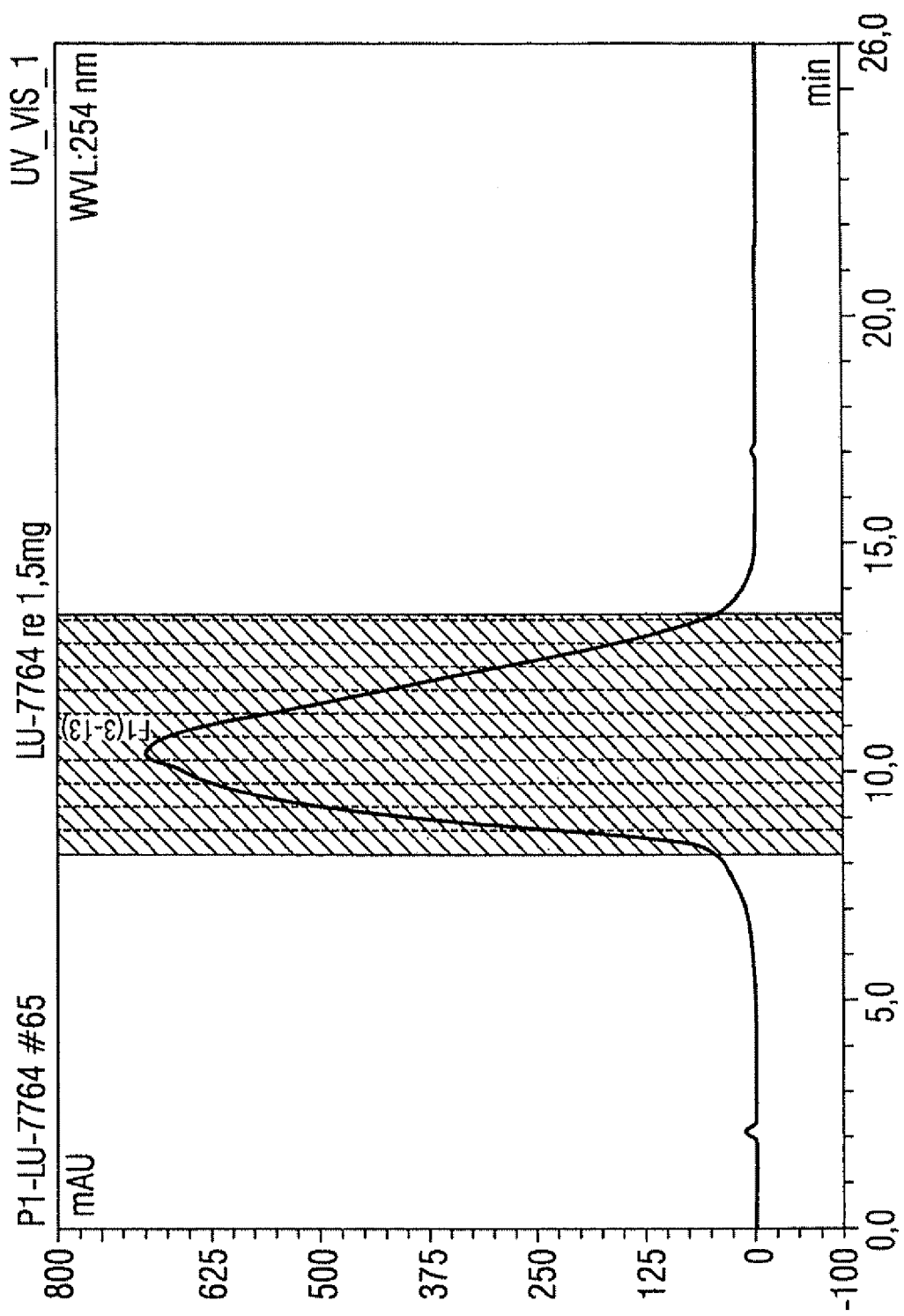
FIG. 3 shows the chromatogram of FIG. 2, the collected fractions being highlighted in grey.

FIGS. 2 and 3 show the corresponding chromatograms for the separation of luciferase mRNA on a preparative scale (1.5 mg), wherein the gradient program is shown in broken lines in FIG. 2. The collected fractions 1 to 10 are highlighted in grey in FIGS. 2 and 3; the fractions were collected over a period of 1 minute.

In each case 1 µg of the luciferase mRNA from collected fractions 2 to 10 was applied onto an agarose gel and visualised with the assistance of ethidium bromide, in order to determine the purity of the mRNA fraction.

Figure 4:
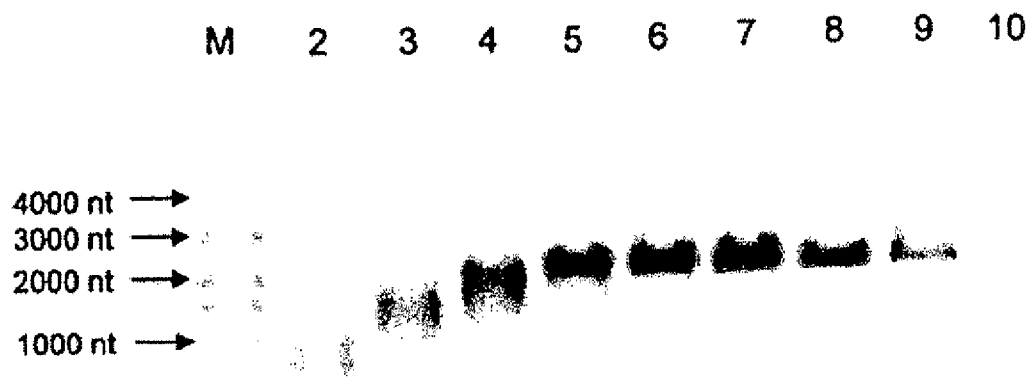
FIG. 4 shows verification of the purity of the collected mRNA fractions on an agarose gel.

The result of the agarose gel separation is shown in FIG. 4 (M denotes a size standard). Fractions 5 to 8 contain the desired luciferase mRNA without undesired impurities. As a result, a separation of the RNA was successful, leading to a highly pure fraction of RNA in preparative scale.

This exemplary embodiment shows that, using the method according to the invention, it is possible to purify mRNA on a preparative scale by means of HPLC.

EXAMPLE 2

Separation of 200 μg of a 2 kb and of a 4 kb RNA Fragment with a Stationary Phase, which has a Pore Size of 1000 Å

200 μg of a 2 kb and 4 kb RNA fragment were used for separation. A porous, non-alkylated polystyrene/divinylbenzene matrix (conventional commercial product from Polymer Laboratories) was used as the stationary phase. It had a particle size of 8 μm and a pore size of 1000 Å. The column used was 2.5 cm long and had a diameter of 4.6 mm. The sampler temperature was 12° C., the temperature for the HPLC separation, in particular of the separation column, was 78° C., i.e. operations were carried out under completely denaturing conditions.
Separation Proceeds Via a Gradient Program
    Eluent A: 0.1 M triethylammonium acetate
    Eluent B: 0.1 M triethylammonium acetate/25% acetonitrile
    Eluent composition:
        starting level: 62% A and 38% B (1st-3rd min)
        separation range I: gradient 38%-49.5% B (5.75% increase in B/min) (3rd-5th min)
        separation range II: gradient 49.5%-57% B (0.83% increase in B/min) (5th-14th min)
        rinsing range: 100% B (15th-20th min)
Detection proceeded with a UV detector at 254 nm with a reference measurement at 600 nm. Flow rate was 3 ml/min.

Figure 5:
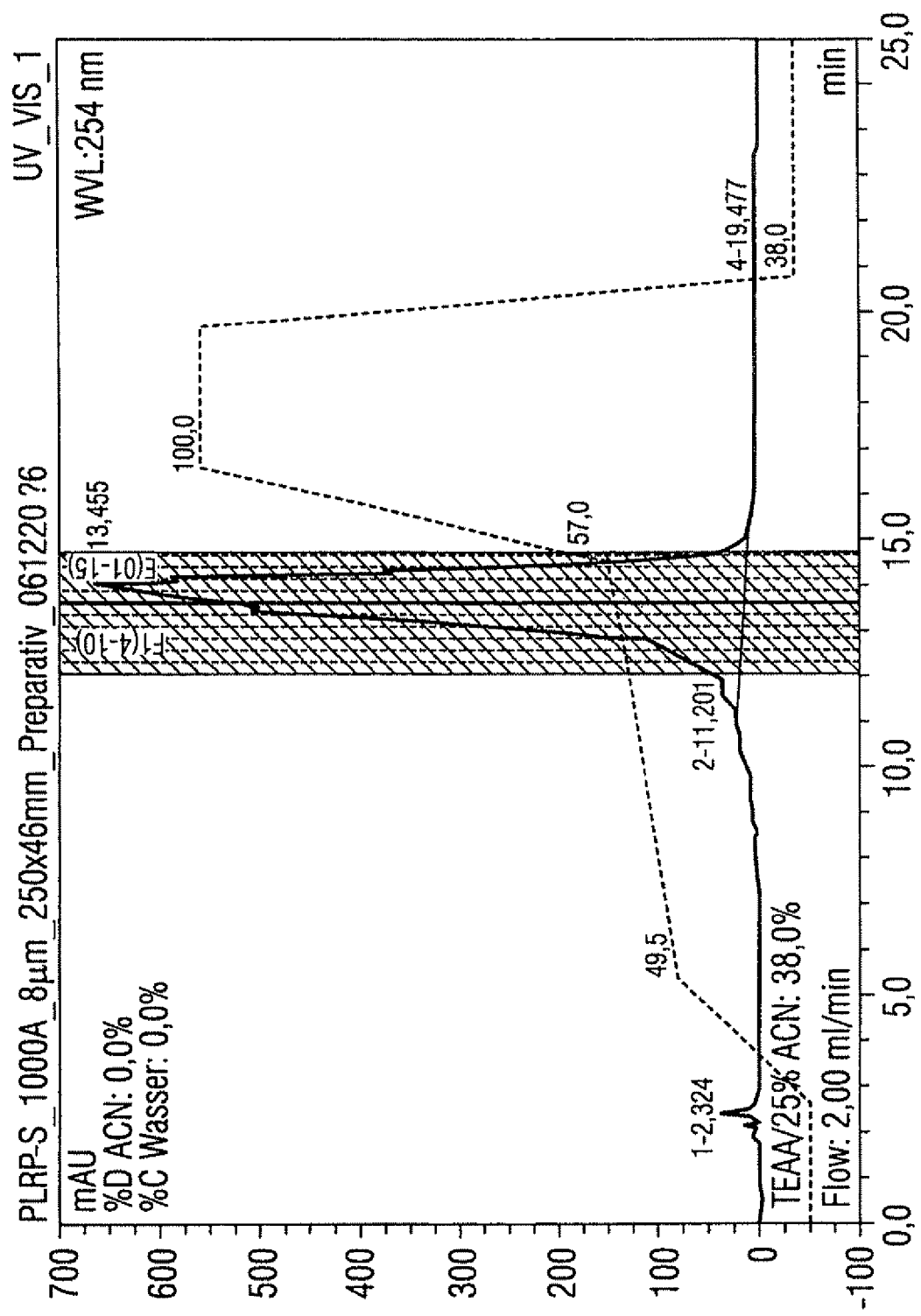
FIG. 5 shows a chromatogram of a separation of 200 µg of a 2 kb and of a 4 kb RNA fragment with a stationary phase, which has a pore size of 1000 Å.

FIG. 5 shows the corresponding chromatograms for this separation on a preparative scale (200 μg), wherein the gradient program is shown in broken lines in FIG. 5. The collected fractions are highlighted in grey in FIG. 5; the fractions were collected over a period of 1 minute. As a result, a separation of the RNA was successful, leading to a highly pure fraction of RNA in preparative scale.

EXAMPLE 3

Separation of 100 μg of a 2 kb and of a 4 kb RNA Fragment with a Stationary Phase, which has a Pore Size of 4000 Å

100 μg of a 2 kb and 4 kb RNA fragment were used for separation. A porous, non-alkylated polystyrene/divinylbenzene matrix (conventional commercial product from Polymer Laboratories) was used as the stationary phase. It had a particle size of 8 μm and a pore size of 4000 Å. The column used was 2.5 cm long and had a diameter of 4.6 mm. The sampler temperature was 12° C., the temperature for the HPLC separation, in particular of the separation column, was 78° C., i.e. operations were carried out under completely denaturing conditions.
Separation Proceeds Via a Gradient Program
    Eluent A: 0.1 M triethylammonium acetate
    Eluent B: 0.1 M triethylammonium acetate/25% acetonitrile
    Eluent composition:
        starting level: 62% A and 38% B (1st-3rd min)
        separation range I: gradient 38%-49.5% B (5.75% increase in B/min) (3rd-5th min)
        separation range II: gradient 49.5%-57% B (0.83% increase in B/min) (5th-14th min)
        rinsing range: 100% B (15th-20th min)
Detection proceeded with a UV detector at 254 nm with a reference measurement at 600 nm. Flow rate was 3 ml/min.

Figure 6:
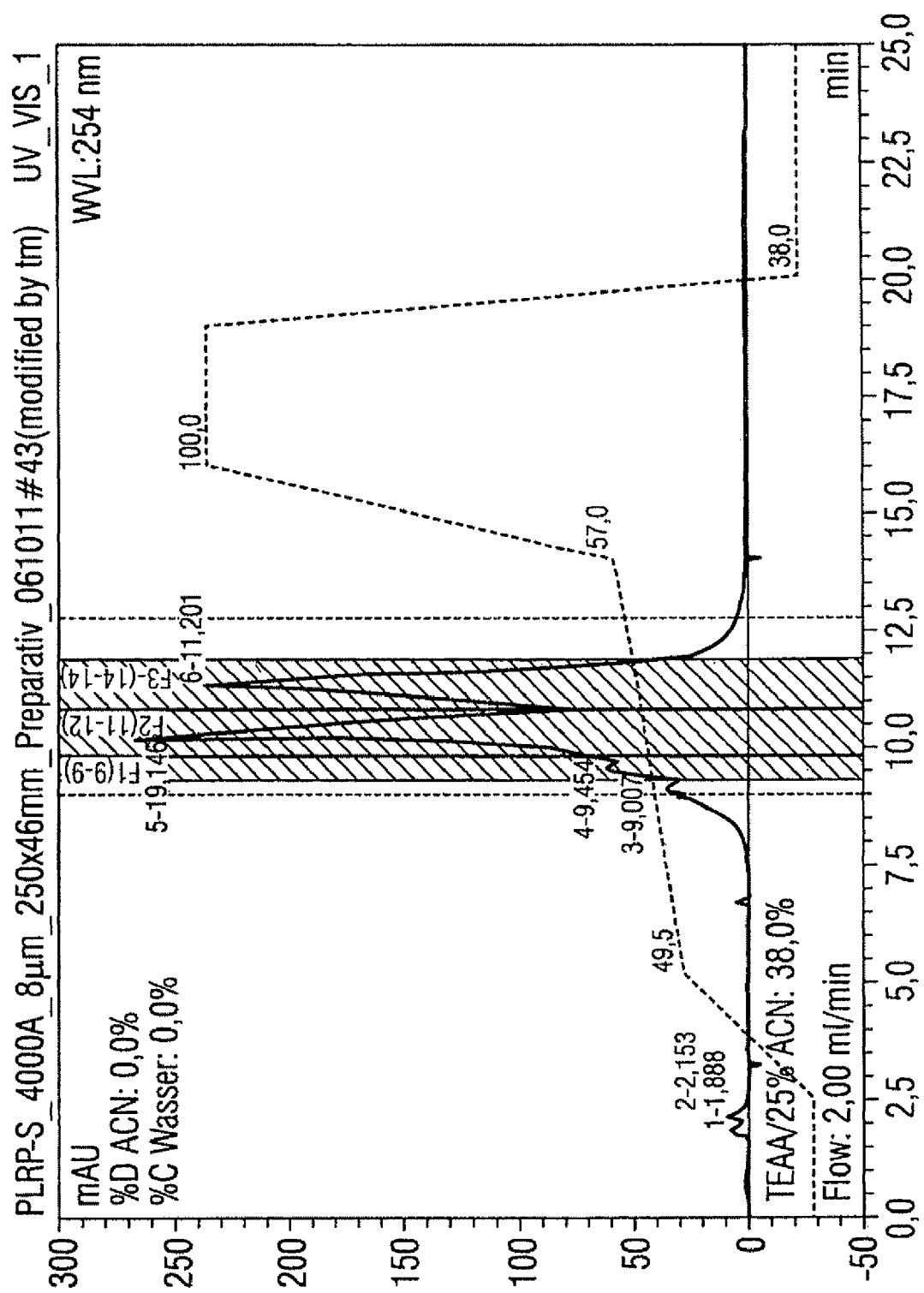
FIG. 6 shows a chromatogram of a separation of 100 µg of a 2 kb and of a 4 kb RNA fragment with a stationary phase, which has a pore size of 4000 Å.

FIG. 6 shows the corresponding chromatograms for this separation on a preparative scale (100 μg), wherein the gradient program is shown in broken lines in FIG. 6. The fractions collected are highlighted in grey in FIG. 6. As a result, a separation of the RNA was successful, leading to a highly pure fraction of RNA in preparative scale.

EXAMPLE 4

Separation of 250 μg of a 2 kb and of a 4 kb RNA Fragment with a Stationary Phase, which has a Pore Size of 4000 Å

250 μg of a 2 kb and 4 kb RNA fragment were used for separation. A porous, non-alkylated polystyrene/divinylbenzene matrix (conventional commercial product from Polymer Laboratories) was used as the stationary phase. It had a particle size of 8 μm and a pore size of 4000 Å. The column used was 2.5 cm long and had a diameter of 4.6 mm. The sampler temperature was 12° C., the temperature for the HPLC separation, in particular of the separation column, was 78° C., i.e. operations were carried out under completely denaturing conditions.
Separation Proceeds Via a Gradient Program
    Eluent A: 0.1 M triethylammonium acetate
    Eluent B: 0.1 M triethylammonium acetate/25% acetonitrile
    Eluent composition:
        starting level: 62% A and 38% B (1st-3rd min)
        separation range I: gradient 38%-49.5% B (5.75% increase in B/min) (3rd-5th min)
        separation range II: gradient 49.5%-57% B (0.83% increase in B/min) (5th-14th min)
        rinsing range: 100% B (15th-20th min)
Detection proceeded with a UV detector at 254 nm with a reference measurement at 600 nm. Flow rate was 3 ml/min.

Figure 7:
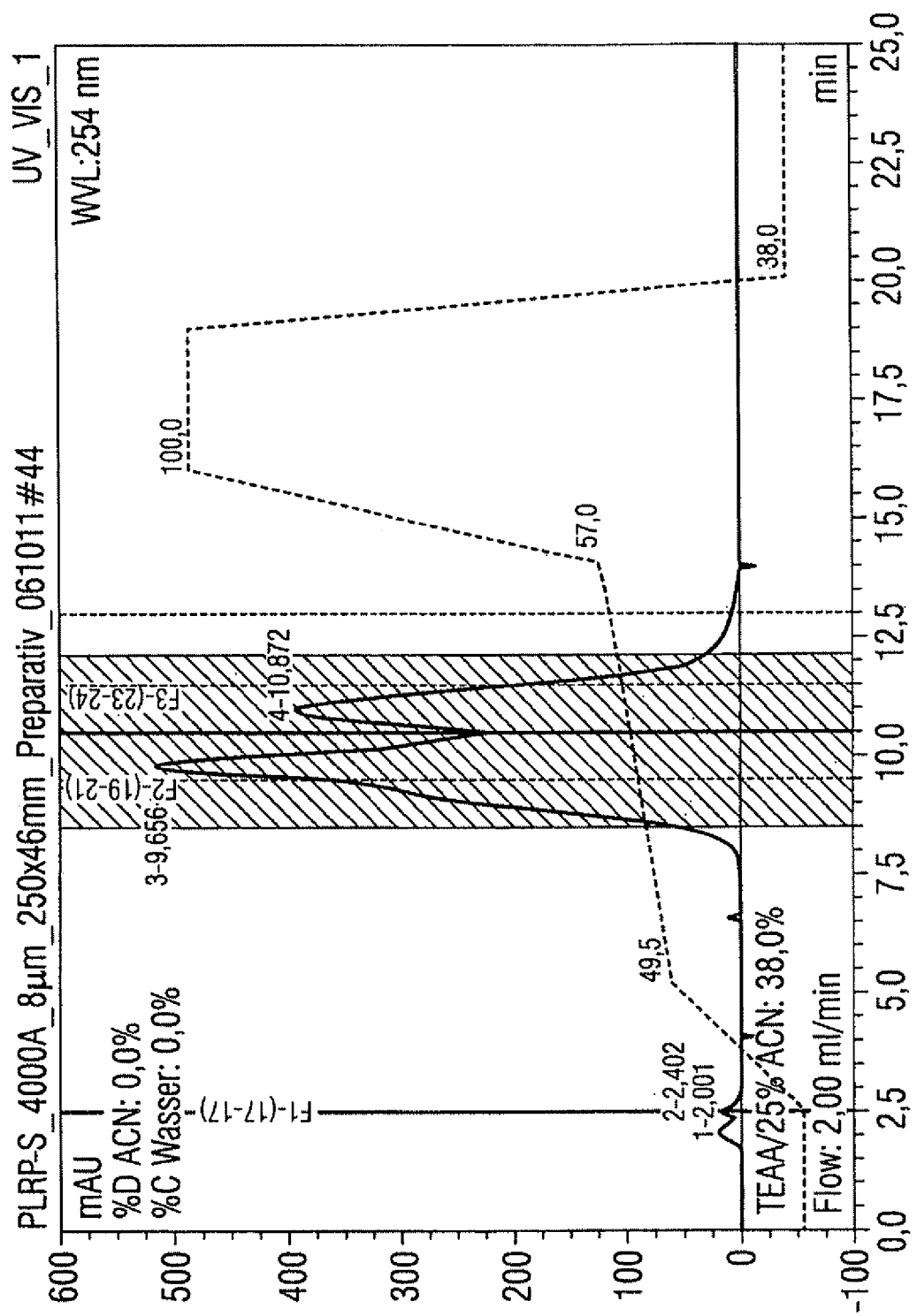
FIG. 7 shows a chromatogram of a separation of 250 µg of a 2 kb and of a 4 kb RNA fragment with a stationary matrix, which has a pore size of 4000 Å.

FIG. 7 shows the corresponding chromatograms for this separation on a preparative scale (250 μg), wherein the gradient program is shown in broken lines in FIG. 7. The fractions collected are highlighted in grey in FIG. 7. As a result, a separation of the RNA was successful, leading to a highly pure fraction of RNA in preparative scale.

Figure 8:
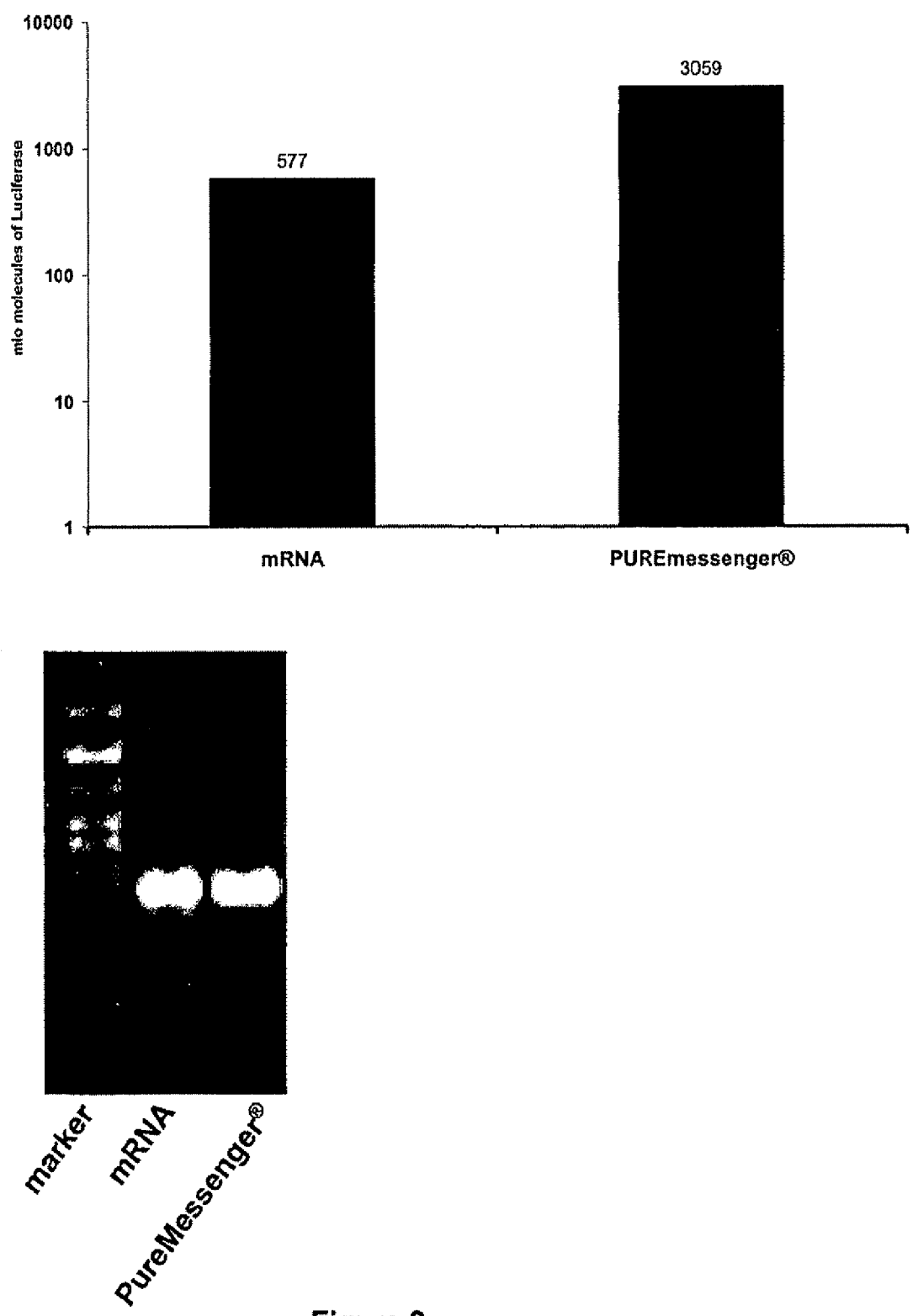
FIG. 8 is a bar chart which demonstrates the improvement in the expression of luciferase from RNA purified with the method according to the invention.

The improvement of the expression of luciferase resulting from purification with the method according to the invention is shown in FIG. 8.

EXAMPLE 5

Separation of 3 mg of a 1.7 kb RNA (FliC(GC)-Preparation, FC9050) with a Stationary Phase, which has a Pore Size of 4000 Å

3 mg of a 1.7 kb RNA (FliC(GC)-preparation, FC9050) were used for separation. A porous, non-alkylated polystyrene/divinylbenzene matrix (conventional commercial product from Polymer Laboratories) was used as the stationary phase. It had a particle size of 8 μm and a pore size of 4000 Å. The column used was 2.5 cm long and had a diameter of 4.6 mm. The sampler temperature was 12° C., the temperature for the HPLC separation, in particular of the separation column, was 78° C., i.e. operations were carried out under completely denaturing conditions.

Separation Proceeds Via a Gradient Program
Eluent A: 0.1 M triethylammonium acetate
Eluent B: 0.1 M triethylammonium acetate/25% acetonitrile
Eluent composition:
starting level: 62% A and 38% B (1st-3rd min)
separation range I: gradient 38%-49.5% B (5.75% increase in B/min) (3rd-5th min)
separation range II: gradient 49.5%-57% B (0.83% increase in B/min) (5th-14th min)
rinsing range: 100% B (15th-20th min)

Detection proceeded with a UV detector at 254 nm with a reference measurement at 600 nm. Flow rate was 3 ml/min.

FIG. 10 shows the corresponding chromatograms for this separation on a preparative scale (3 mg), wherein the gradient program is shown in broken lines in FIG. 10. The fractions collected are highlighted in grey in FIG. 10. As can be seen, a separation of the RNA was successful, leading to a highly pure fraction of RNA in preparative scale.

EXAMPLE 6

Separation of 1.5 mg of a FOLH1(GC) RNA Preparation (FO-9334), 1.5 Mg of a KLK3(GC) RNA Preparation (KL-8849), 1.5 mg of a PSCA(GC) RNA Preparation (PS-8845) or 1.5 mg of a STEAP (GC) RNA Preparation (ST-8848) with a Stationary Phase, which has a Pore Size of 4000 Å

1.5 mg of a FOLH1 (GC) RNA preparation (FO-9334), 1.5 mg of a KLK3(GC) RNA preparation (KL-8849), 1.5 mg of a PSCA(GC) RNA preparation (PS-8845) or 1.5 mg of a STEAP(GC) RNA preparation (ST-8848) were used for separation. A porous, non-alkylated polystyrene/divinylbenzene matrix (conventional commercial product from Polymer Laboratories) was used as the stationary phase. It had a particle size of 8 μm and a pore size of 4000 Å. The column used was 2.5 cm long and had a diameter of 4.6 mm. The sampler temperature was 12° C., the temperature for the HPLC separation, in particular of the separation column, was 78° C., i.e. operations were carried out under completely denaturing conditions.

Separation Proceeds Via a Gradient Program
Eluent A: 0.1 M triethylammonium acetate
Eluent B: 0.1 M triethylammonium acetate/25% acetonitrile
Eluent composition:
starting level: 62% A and 38% B (1st-3rd min)
separation range I: gradient 38%-49.5% B (5.75% increase in B/min) (3rd-5th min)
separation range II: gradient 49.5%-57% B (0.83% increase in B/min) (5th-14th min)
rinsing range: 100% B (15th-20th min)

Detection proceeded with a UV detector at 254 nm with a reference measurement at 600 nm. Flow rate was 3 ml/min.

FIGS. 11, 12, 13 and 14 shows the corresponding chromatograms for this separation of 1.5 mg of a FOLH1(GC) RNA preparation (FO-9334), 1.5 mg of a KLK3(GC) RNA preparation (KL-8849), 1.5 mg of a PSCA(GC) RNA preparation (PS-8845) or 1.5 mg of a STEAP(GC) RNA preparation (ST-8848), respectively on a preparative scale (1.5 mg), wherein the gradient program is shown in broken lines in these Figures. The fractions collected are highlighted in grey in FIGS. 11, 12, 13 and 14. As can be seen, a separation of the RNAs is possible in each case, leading to a highly pure fraction of RNA in each case in preparative scale.

EXAMPLE 7

Separation of a Mixture of 200 μg of a 2 kb RNA and 200 μg of a 4 kb RNA on a Non-Porous Stationary Polystyrenedivinylbenzene Matrix (Comparison Example)

A mixture of 200 μg of a 2 kb RNA and 200 μg of a 4 kb RNA were used for separation. The columns used were packed with either a 1000 Å non-alkylated porous polystyrenedivinylbenzene or a non-porous stationary polystyrenedivinylbenzene matrix. The column used for the 1000 Å non-alkylated porous polystyrenedivinylbenzene was 2.5 cm long and had a diameter of 4.6 mm. The column used for the non-alkylated non-porous polystyrenedivinylbenzene was 2.5 cm long and had a diameter of 4.0 mm. The sampler temperature was 12° C., the temperature for the HPLC separation, in particular of the separation column, was 78° C., i.e. operations were carried out under completely denaturing conditions.

Separation Proceeds Via a Gradient Program
Eluent A: 0.1 M triethylammonium acetate
Eluent B: 0.1 M triethylammonium acetate/25% acetonitrile
Eluent composition:
starting level: 62% A and 38% B (1st-3rd min)
separation range I: gradient 38%-49.5% B (5.75% increase in B/min) (3rd-5th min)
separation range II: gradient 49.5%-57% B (0.83% increase in B/min) (5th-14th min)
rinsing range: 100% B (15th-20th min)

Detection proceeded with a UV detector at 254 nm with a reference measurement at 600 nm. Flow rate was 3 ml/min.

FIG. 15 shows the corresponding chromatogram for this separation on a preparative scale (each 200 μg), wherein the gradient program is shown in broken lines in FIG. 15. The fractions collected are highlighted in grey in FIG. 15. As can be seen, a separation of both RNAs is not possible using a common non-alkylated porous polystyrenedivinylbenzene as a matrix. FIG. 16 shows the agarose gel corresponding to the chromatogram according to FIG. 15.

The invention claimed is:

1. A method for purifying RNA on a preparative scale, wherein the RNA is purified by HPLC or low or normal pressure liquid chromatography using a porous reversed phase as stationary phase and a mobile phase, wherein the porous reversed phase is a porous non-alkylated polystyrene-divinylbenzene.

2. A method according to claim 1, wherein the RNA is selected from among tRNA, rRNA, mRNA or whole-cell RNA, and RNA variants.

3. A method according to claim 1, wherein the RNA has a size of up to about 15000 nucleotides or base pairs.

4. A method according to claim 1, wherein the RNA has a size of up to 100 to 10000 nucleotides or base pairs.

5. A method according to claim 1, wherein the porous reversed phase has a particle size of 8 μm to 50 μm.

6. A method according to claim 1, wherein the reversed phase has a pore size of 1000 Å to 5000 Å.

7. A method according to claim 1, wherein the reversed phase has a pore size of 1000 Å to 4000 Å.

8. A method according to claim 1, wherein the porous reversed phase is formed by beads or occurs as a polymerized block.

9. A method according to claim 1, wherein the HPLC column has a length of more than 5 cm up to 100 cm and a diameter of more than 4 mm up to 1 m.

10. A method according to claim 1, wherein HPLC purification is performed as an ion pair method, an ion with positive charge being added to the mobile phase as counterion to the negatively charged RNA, or by size exclusion chromatography, gel filtration, affinity chromatography, hydrophobic interaction chromatography or ion pair chromatography.

11. A method according to claim 1, wherein a mixture of an aqueous solvent and an organic solvent is used for HPLC purification in the mobile phase for the purpose of elution.

12. A method according to claim 11, wherein the aqueous solvent is a buffer.

13. A method according to claim 12, wherein the buffer is selected from the group consisting of triethylammonium acetate, trifluoroacetic acid, acetic acid, formic acid, acetate buffer, phosphate buffer, tetrabutylammonium bisulfate, tetrabutylammonium bromide and tetrabutylammonium chloride.

14. A method according to claim 13, wherein the triethylammonium acetate buffer is a 0.1 M triethylammonium acetate buffer.

15. A method according to claim 11, wherein the organic solvent is acetonitrile, methanol, ethanol, 1-propanol, 2-propanol and acetone or a mixture thereof.

16. A method according to claim 15, wherein the organic solvent is acetonitrile.

17. A method according to claim 11, wherein the mixture of an aqueous solvent and an organic solvent comprises 0.1 M triethylammonium acetate and acetonitrile.

18. A method according to claim 11, wherein the mixture of an aqueous solvent and an organic solvent consists of 5.0 vol. % to 25.0 vol. % organic solvent the aqueous solvent.

19. A method according to claim 18, wherein the mixture of an aqueous solvent and an organic solvent consists of 7.5 vol. % to 17.5 vol. % organic solvent the aqueous solvent.

20. A method according to claim 11, wherein the elution proceeds isocratically.

21. A method according to claim 1, wherein a gradient separation proceeds.

22. A method according to claim 21, wherein, in the event of gradient separation, the proportion of organic solvent is increased by at least 10% relative to the initial vol. % in the mobile phase.

23. A method according to claim 22, wherein the proportion of organic solvent in the mobile phase in the course of HPLC separation amounts to from 3 to 9 vol. %.

24. A method according to claim 22, wherein the proportion of organic solvent in the mobile phase is increased in the course of HPLC separation from 3 to 9 vol. %, in each case relative to the mobile phase.

25. A method according to claim 24, wherein the proportion of organic solvent in the mobile phase is increased in the course of HPLC separation from 6.5 to 8.5 vol. %, in each case relative to the mobile phase.

26. A method according to claim 1, wherein the RNA is purified by HPLC using a porous reversed phase as stationary phase, wherein the porous reversed phase is a porous non-alkylated polystyrenedivinylbenzene.

* * * * *

SEQUENCE LISTING

<160> NUMBER OF SEQ ID NOS: 1

<210> SEQ ID NO 1
<211> LENGTH: 1825
<212> TYPE: RNA
<213> ORGANISM: Artificial Sequence
<220> FEATURE:
<223> OTHER INFORMATION: Luciferase wild type, CAP-Ppluc(wt)-muag-A70 from Figure 9

```
<400> SEQUENCE: 1
gggagaaagc uuggcauucc gguacuguug guaaagccac cauggaagac gccaaaaaca      60
uaaagaaagg cccggcgcca uucuauccgc uggaagaugg aaccgcugga gagcaacugc     120
auaaggcuau gaagagauac gcccugguuc cuggaacaau ugcuuuuaca gaugcacaua     180
ucgaggugga caucacuuac gcugaguacu ucgaaauguc cguucgguug gcagaagcua     240
ugaaacgaua ugggcugaau acaaaucaca gaaucgucgu augcagugaa aacucucuuc     300
aauucuuuau gccggguguug ggcgcguuau uuaucgagu ugcaguugcg cccgcgaacg     360
acauuuauaa ugaacgugaa uugcucaaca guaugggcau uucgcagccu accguggugu     420
ucguuuccaa aagggguug caaaaaauuu ugaacgugca aaaaaagcuc ccaaucaucc     480
aaaaaauuau uaucauggau ucuaaaacgg auuaccaggg auuucagucg auguacacgu     540
ucgucacauc ucaucuaccu cccguuuua augaauacga uuuugugcca gaguccuucg     600
auagggacaa gacaauugca cugaucauga acuccucugg aucuacuggu cugccuaaag     660
gugucgcucu gccucauaga acugccugcg ugagauucuc gcaugccaga gauccuauuu     720
uuggcaauca aaucauuccg gauacugcga uuuuaagugu uguuccauuc caucacgguu     780
uuggaauguu uacuacacuc ggauauuuga uauguggauu ucgagucguc uuaauguaua     840
gauuugaaga agagcuguuu cugaggagcc uucaggauua caagauucaa agugcgcugc     900
uggugccaac ccuauucucc uucuucgcca aaagcacucu gauugacaaa uacgauuuau     960
cuaauuuaca cgaaauugcu ucugguggcg cucccccucu uaaggaaguc ggggaagcgg    1020
uugccaagag guuccaucug ccagguauca ggcaaggaua ugggcucacu gagacuacau    1080
cagcuauucu gauuacaccc gaggggggau auaaaccggg cgcggucggu aaaguuguuc    1140
cauuuuuuga agcgaagguu guggaucugg auaccgggaa aacgcugggc guuaaucaaa    1200
gaggcgaacu gugugugaga gguccuauga uuaugccgg uuauguaaac aauccggaag    1260
cgaccaacgc cuugauugac aaggauggau ggcuacauuc uggagacaua gcuuacuggg    1320
acgaagacga acacuucuuc aucguugacc gccugaaguc ucugauuaag uacaaaggcu    1380
aucagguggc ucccgcugaa uuggaaucca ucuugcucca acaccccaac aucuucgacg    1440
caggugucgc aggucuucc gacgaugacg ccggugaacu ucccgccgcc guuguuguuu    1500
uggagcacgg aaagacgaug acggaaaaag agaucgugga uuacgucgcc agucaaguaa    1560
caaccgcgaa aaaguugcgc ggaggaguug uguuugugga cgaaguaccg aaaggucuua    1620
ccggaaaacu cgacgcaaga aaaaucagag agauccucau aaaggccaag aagggcggaa    1680
agaucgccgu guaauucuag uuauaagacu gacuagcccg augggccucc caacgggccc    1740
uccuccccuc cuugcaccga gaaaaaaaaa aaaaaaaaa aaaaaaaaaa aaaaaaaaaa    1800
aaaaaaaaaa aaaaaaaaaa aaaaa                                          1825
```